United States Patent
Blanquart

(10) Patent No.: US 9,622,650 B2
(45) Date of Patent: Apr. 18, 2017

(54) SYSTEM AND METHOD FOR SUB-COLUMN PARALLEL DIGITIZERS FOR HYBRID STACKED IMAGE SENSOR USING VERTICAL INTERCONNECTS

(75) Inventor: Laurent Blanquart, Westlake Village, CA (US)

(73) Assignee: DePuy Synthes Products, Inc., Raynham, MA (US)

(*) Notice: Subject to any disclaimer, the term of this patent is extended or adjusted under 35 U.S.C. 154(b) by 1063 days.

(21) Appl. No.: 13/471,432

(22) Filed: May 14, 2012

(65) Prior Publication Data

US 2013/0126709 A1 May 23, 2013

Related U.S. Application Data

(60) Provisional application No. 61/485,432, filed on May 12, 2011, provisional application No. 61/485,435, (Continued)

(51) Int. Cl.
*H01L 27/00* (2006.01)
*H01J 40/14* (2006.01)
(Continued)

(52) U.S. Cl.
CPC .......... *A61B 1/051* (2013.01); *A61B 1/00009* (2013.01); *A61B 1/0676* (2013.01); *H01L 24/17* (2013.01); *H01L 27/146* (2013.01); *H01L 27/1464* (2013.01); *H01L 27/1469* (2013.01); *H01L 27/14601* (2013.01); *H01L 27/14603* (2013.01); *H01L 27/14618* (2013.01); *H01L 27/14634* (2013.01); *H01L 27/14636* (2013.01); *H01L 27/14638* (2013.01); *H01L 27/14641* (2013.01); *H01L 27/14643* (2013.01); *H01L 27/14689* (2013.01); *H04N 5/2256* (2013.01); *H04N 5/378* (2013.01); *H04N 5/3742* (2013.01); *H04N 5/37455* (2013.01); *H04N 5/37457* (2013.01); *H01L 31/028* (2013.01); *H01L 31/0296* (2013.01);
(Continued)

(58) Field of Classification Search
USPC ...................... 250/208.1, 214.1, 214 R, 239; 348/272–283, 294–324; 257/414, 257/431–466
See application file for complete search history.

(56) References Cited

U.S. PATENT DOCUMENTS 3,796,220 A 3/1974 Bredemeier
3,858,577 A 1/1975 Bass et al.
(Continued)

FOREIGN PATENT DOCUMENTS

AU 2012253261 6/2016
CN 1953193 A 4/2007
(Continued)

OTHER PUBLICATIONS

H.Kurino et al., Intelligent image sensor chip with three dimensional structure, Technical Digest, International Electron Devices Meeting 1999, Dec. 5, 1999, pp. 879-882.

*Primary Examiner* — Pascal M Bui-Pho
(74) *Attorney, Agent, or Firm* — Terrence J. Edwards; TechLaw Ventures, PLLC

(57) ABSTRACT

Embodiments of a hybrid imaging sensor and methods for pixel sub-column data read from the within a pixel array.

27 Claims, 20 Drawing Sheets

Related U.S. Application Data filed on May 12, 2011, provisional application No. 61/485,440, filed on May 12, 2011, provisional application No. 61/485,426, filed on May 12, 2011.

(51) Int. Cl.

| | | |
|---|---|---|
| *A61B 1/05* | (2006.01) | |
| *H01L 27/146* | (2006.01) | |
| *A61B 1/00* | (2006.01) | |
| *H04N 5/374* | (2011.01) | |
| *H04N 5/3745* | (2011.01) | |
| *H04N 5/378* | (2011.01) | |
| *H01L 23/00* | (2006.01) | |
| *A61B 1/06* | (2006.01) | |
| *H04N 5/225* | (2006.01) | |
| *H01L 31/028* | (2006.01) | |
| *H01L 31/0296* | (2006.01) | |
| *H01L 31/0304* | (2006.01) | |

(52) U.S. Cl.
CPC .. *H01L 31/0304* (2013.01); *H01L 2924/0002* (2013.01); *H01L 2924/381* (2013.01); *H04N 2005/2255* (2013.01)

(56) References Cited

U.S. PATENT DOCUMENTS

| | | |
|---|---|---|
| 4,011,403 A | 3/1977 | Epstein et al. |
| 4,153,356 A | 5/1979 | Hama |
| 4,350,150 A | 9/1982 | Kubota et al. |
| 4,363,963 A | 12/1982 | Ando |
| 4,429,686 A | 2/1984 | Hosoda |
| 4,433,675 A | 2/1984 | Konoshima |
| 4,436,095 A | 3/1984 | Kruger |
| 4,561,430 A | 12/1985 | Walsh |
| 4,572,164 A | 2/1986 | Yoshida et al. |
| 4,589,404 A | 5/1986 | Barath et al. |
| 4,600,940 A | 7/1986 | Sluyter |
| 4,604,992 A | 8/1986 | Sato |
| 4,670,653 A | 6/1987 | McConkle et al. |
| 4,740,837 A | 4/1988 | Yanagisawa et al. |
| 4,741,327 A | 5/1988 | Yabe |
| 4,745,471 A | 5/1988 | Takamura et al. |
| 4,773,396 A | 9/1988 | Okazaki |
| 4,786,965 A | 11/1988 | Yabe |
| 4,800,424 A | 1/1989 | Noguchi |
| 4,831,444 A | 5/1989 | Kato |
| 4,832,003 A | 5/1989 | Yabe |
| 4,845,555 A | 7/1989 | Yabe et al. |
| 4,853,772 A | 8/1989 | Kikuchi |
| 4,866,526 A | 9/1989 | Ams et al. |
| 4,888,639 A | 12/1989 | Yabe et al. |
| 4,918,521 A | 4/1990 | Yabe et al. |
| 4,938,205 A | 7/1990 | Nudelman |
| 4,942,473 A | 7/1990 | Zeevi et al. |
| 4,953,539 A | 9/1990 | Nakamura et al. |
| 4,954,878 A | 9/1990 | Fox et al. |
| 5,010,038 A | 4/1991 | Fox et al. |
| 5,010,876 A | 4/1991 | Henley et al. |
| 5,016,975 A | 5/1991 | Sasaki et al. |
| 5,021,888 A | 6/1991 | Kondou et al. |
| 5,042,915 A | 8/1991 | Akutsu et al. |
| RE33,854 E | 3/1992 | Adair |
| 5,103,497 A | 4/1992 | Hicks |
| 5,111,804 A | 5/1992 | Funakoshi |
| 5,115,309 A | 5/1992 | Hang |
| 5,133,035 A | 7/1992 | Hicks |
| 5,168,361 A | 12/1992 | Hackmann |
| 5,168,863 A | 12/1992 | Kurtzer |
| 5,187,572 A | 2/1993 | Nakamura et al. |
| 5,188,094 A | 2/1993 | Adair |
| 5,200,838 A | 4/1993 | Nudelman et al. |
| 5,220,198 A | 6/1993 | Tsuji |
| 5,227,662 A | 7/1993 | Ohno et al. |
| 5,228,430 A | 7/1993 | Sakamoto |
| 5,237,403 A | 8/1993 | Sugimoto et al. |
| 5,241,170 A | 8/1993 | Field, Jr. et al. |
| 5,277,172 A | 1/1994 | Sugimoto |
| 5,289,555 A | 2/1994 | Sanso |
| 5,307,804 A | 5/1994 | Bonnet |
| 5,313,306 A | 5/1994 | Kuban et al. |
| 5,325,847 A | 7/1994 | Matsuno |
| 5,339,275 A | 8/1994 | Hyatt |
| 5,381,784 A | 1/1995 | Adair |
| 5,400,267 A | 3/1995 | Denen et al. |
| 5,402,768 A | 4/1995 | Adair |
| 5,411,020 A | 5/1995 | Ito |
| 5,427,087 A | 6/1995 | Ito et al. |
| 5,454,366 A | 10/1995 | Ito et al. |
| 5,461,425 A | 10/1995 | Fowler et al. |
| 5,471,515 A | 11/1995 | Fossum et al. |
| 5,489,801 A | 2/1996 | Blish, II |
| 5,494,483 A | 2/1996 | Adair |
| 5,522,006 A | 5/1996 | Takeuchi et al. |
| 5,550,595 A | 8/1996 | Hannah |
| 5,576,781 A | 11/1996 | Deleeuw |
| 5,594,282 A | 1/1997 | Otsuki |
| 5,594,497 A | 1/1997 | Ahern et al. |
| 5,614,763 A | 3/1997 | Womack |
| 5,665,959 A | 9/1997 | Fossum et al. |
| 5,734,418 A | 3/1998 | Danna |
| 5,748,234 A | 5/1998 | Lippincott |
| 5,754,313 A | 5/1998 | Pelchy et al. |
| 5,757,075 A | 5/1998 | Kitaoka |
| 5,784,099 A | 7/1998 | Lippincott |
| 5,841,126 A | 11/1998 | Fossum et al. |
| 5,857,963 A | 1/1999 | Pelchy et al. |
| 5,879,289 A | 3/1999 | Yarush et al. |
| 5,887,049 A | 3/1999 | Fossum |
| 5,896,166 A | 4/1999 | D'Alfonso et al. |
| 5,907,178 A | 5/1999 | Baker et al. |
| 5,929,901 A | 7/1999 | Adair et al. |
| 5,949,483 A | 9/1999 | Fossum et al. |
| 5,986,693 A | 11/1999 | Adair et al. |
| 5,990,506 A | 11/1999 | Fossum et al. |
| 6,005,619 A | 12/1999 | Fossum |
| 6,021,172 A | 2/2000 | Fossum et al. |
| 6,027,955 A | 2/2000 | Lee et al. |
| 6,028,330 A | 2/2000 | Lee et al. |
| 6,043,839 A | 3/2000 | Adair et al. |
| 6,059,776 A | 5/2000 | Gatto |
| 6,059,793 A | 5/2000 | Pagedas |
| 6,073,043 A | 6/2000 | Schneider |
| 6,096,573 A | 8/2000 | Chen |
| 6,101,232 A | 8/2000 | Fossum et al. |
| 6,118,142 A | 9/2000 | Chen et al. |
| 6,139,489 A | 10/2000 | Wampler et al. |
| 6,142,930 A | 11/2000 | Ito et al. |
| 6,166,367 A | 12/2000 | Cho |
| 6,166,768 A | 12/2000 | Fossum et al. |
| 6,180,969 B1 | 1/2001 | Yang et al. |
| 6,184,055 B1 | 2/2001 | Yang et al. |
| 6,194,260 B1 | 2/2001 | Chien et al. |
| 6,198,087 B1 | 3/2001 | Boon |
| 6,207,984 B1 | 3/2001 | Chang |
| 6,211,904 B1 | 4/2001 | Adair et al. |
| 6,215,517 B1 | 4/2001 | Takahashi et al. |
| 6,239,456 B1 | 5/2001 | Berezin et al. |
| 6,242,277 B1 | 6/2001 | Lin et al. |
| 6,255,681 B1 | 7/2001 | Pan |
| 6,272,269 B1 | 8/2001 | Naum |
| 6,275,255 B1 | 8/2001 | Adair et al. |
| 6,294,775 B1 | 9/2001 | Seibel et al. |
| 6,303,421 B1 | 10/2001 | Chang |
| 6,310,642 B1 | 10/2001 | Adair et al. |
| 6,313,868 B1 | 11/2001 | D'Alfonso et al. |
| 6,320,630 B1 | 11/2001 | Yamashita et al. |
| 6,327,493 B1 | 12/2001 | Ozawa et al. |
| 6,331,156 B1 | 12/2001 | Haefele et al. |
| 6,333,205 B1 | 12/2001 | Rhodes |
| 6,387,043 B1 | 5/2002 | Yoon |
| 6,388,243 B1 | 5/2002 | Berezin et al. |
| 6,390,972 B1 | 5/2002 | Speier et al. |

(56) References Cited

U.S. PATENT DOCUMENTS

| | | |
|---|---|---|
| 6,400,824 B1 | 6/2002 | Mansoorian et al. |
| 6,404,048 B2 | 6/2002 | Akram |
| 6,410,377 B1 | 6/2002 | Hwang et al. |
| 6,416,463 B1 | 7/2002 | Tsuzuki et al. |
| 6,419,626 B1 | 7/2002 | Yoon |
| 6,424,369 B1 | 7/2002 | Adair et al. |
| 6,436,032 B1 | 8/2002 | Eto et al. |
| 6,441,482 B1 | 8/2002 | Foster |
| 6,452,626 B1 | 9/2002 | Adair et al. |
| 6,456,326 B2 | 9/2002 | Fossum et al. |
| 6,469,739 B1 | 10/2002 | Bechtel et al. |
| 6,485,414 B1 | 11/2002 | Neuberger |
| 6,512,280 B2 | 1/2003 | Chen et al. |
| 6,515,321 B1 | 2/2003 | Jwo |
| 6,549,235 B1 | 4/2003 | Fossum et al. |
| 6,555,842 B1 | 4/2003 | Fossum et al. |
| 6,570,617 B2 | 5/2003 | Fossum et al. |
| 6,588,884 B1 | 7/2003 | Furlani et al. |
| 6,606,122 B1 | 8/2003 | Shaw et al. |
| 6,610,557 B2 | 8/2003 | Lee et al. |
| 6,627,474 B2 | 9/2003 | Barna et al. |
| 6,659,940 B2 | 12/2003 | Adler |
| 6,665,013 B1 | 12/2003 | Fossum et al. |
| 6,690,466 B2 | 2/2004 | Miller et al. |
| 6,692,431 B2 | 2/2004 | Kazakevich |
| 6,704,049 B1 | 3/2004 | Fossum |
| 6,720,810 B1 | 4/2004 | New |
| 6,726,620 B2 | 4/2004 | Shibata et al. |
| 6,730,900 B2 | 5/2004 | Hsish et al. |
| 6,740,870 B1 | 5/2004 | Doudoumopoulos |
| 6,744,068 B2 | 6/2004 | Fossum et al. |
| 6,773,392 B2 | 8/2004 | Kikuchi et al. |
| 6,784,940 B1 | 8/2004 | Takazawa et al. |
| 6,796,939 B1 | 9/2004 | Hirata et al. |
| 6,799,065 B1 | 9/2004 | Niemeyer |
| 6,809,358 B2 | 10/2004 | Hsieh et al. |
| 6,812,949 B1 | 11/2004 | Switzer et al. |
| 6,838,653 B2 | 1/2005 | Campbell et al. |
| 6,838,716 B2 | 1/2005 | Asada et al. |
| 6,856,712 B2 | 2/2005 | Fauver et al. |
| 6,862,036 B2 | 3/2005 | Adair et al. |
| 6,879,340 B1 | 4/2005 | Chevallier |
| 6,897,082 B2 | 5/2005 | Rhodes et al. |
| 6,899,675 B2 | 5/2005 | Cline et al. |
| 6,921,920 B2 | 7/2005 | Kazakevich |
| 6,943,838 B2 | 9/2005 | Fossum et al. |
| 6,947,090 B2 | 9/2005 | Komoro et al. |
| 6,961,461 B2 | 11/2005 | MacKinnon et al. |
| 6,970,195 B1 | 11/2005 | Bidermann et al. |
| 6,976,954 B2 | 12/2005 | Takahashi |
| 6,977,733 B2 | 12/2005 | Denk et al. |
| 6,982,740 B2 | 1/2006 | Adair et al. |
| 6,982,742 B2 | 1/2006 | Adair et al. |
| 6,997,871 B2 | 2/2006 | Sonnenschein et al. |
| 6,999,118 B2 | 2/2006 | Suzuki |
| 7,002,231 B2 | 2/2006 | Rhodes et al. |
| 7,002,621 B2 | 2/2006 | Adair et al. |
| 7,009,634 B2 | 3/2006 | Iddan et al. |
| 7,009,646 B1 | 3/2006 | Fossum et al. |
| 7,018,331 B2 | 3/2006 | Chang et al. |
| 7,027,092 B2 | 4/2006 | Altree |
| 7,030,904 B2 | 4/2006 | Adair et al. |
| 7,037,259 B2 | 5/2006 | Hakamata et al. |
| 7,061,117 B2 | 6/2006 | Yang et al. |
| 7,068,878 B2 | 6/2006 | Crossman-Bosworth et al. |
| 7,070,560 B2 | 7/2006 | Takashi et al. |
| 7,088,398 B1 | 8/2006 | Wolf et al. |
| 7,102,682 B2 | 9/2006 | Baer |
| 7,105,371 B2 | 9/2006 | Fossum et al. |
| 7,106,367 B2 | 9/2006 | Sarwari |
| 7,106,377 B2 | 9/2006 | Bean et al. |
| 7,115,091 B2 | 10/2006 | Root et al. |
| 7,129,108 B2 | 10/2006 | Jang |
| 7,183,129 B2 | 2/2007 | Lee |
| 7,184,084 B2 | 2/2007 | Glenn |
| 7,189,226 B2 | 3/2007 | Auld et al. |
| 7,193,519 B2 | 3/2007 | Root et al. |
| 7,202,899 B2 | 4/2007 | Lin et al. |
| 7,217,967 B2 | 5/2007 | Han |
| 7,227,469 B2 | 6/2007 | Varner et al. |
| 7,230,615 B2 | 6/2007 | Wang et al. |
| 7,232,712 B2 | 6/2007 | Han |
| 7,244,920 B2 | 7/2007 | Kim et al. |
| 7,250,594 B2 | 7/2007 | Lin et al. |
| 7,258,546 B2 | 8/2007 | Beier et al. |
| 7,258,663 B2 | 8/2007 | Doguchi et al. |
| 7,261,687 B2 | 8/2007 | Yang |
| 7,273,452 B2 | 9/2007 | Barbato et al. |
| 7,274,390 B2 | 9/2007 | Sevat et al. |
| 7,276,785 B2 | 10/2007 | Bauer et al. |
| 7,280,139 B2 | 10/2007 | Pahr et al. |
| 7,282,025 B2 | 10/2007 | Abe |
| 7,283,566 B2 | 10/2007 | Siemens et al. |
| 7,295,578 B1 | 11/2007 | Lyle et al. |
| 7,303,528 B2 | 12/2007 | Couvillon, Jr. |
| 7,317,955 B2 | 1/2008 | McGreevy |
| 7,319,478 B2 | 1/2008 | Dolt et al. |
| 7,331,523 B2 | 2/2008 | Meier et al. |
| 7,338,832 B2 | 3/2008 | Park et al. |
| 7,339,982 B2 | 3/2008 | Wood, Jr. |
| 7,354,841 B2 | 4/2008 | Jeon |
| 7,365,768 B1 | 4/2008 | Ono et al. |
| 7,368,771 B2 | 5/2008 | Roh et al. |
| 7,369,166 B2 | 5/2008 | Fossum et al. |
| 7,369,176 B2 | 5/2008 | Sonnenschein et al. |
| 7,386,084 B2 | 6/2008 | Yin |
| 7,391,013 B2 | 6/2008 | Johnston et al. |
| 7,397,076 B2 | 7/2008 | Jang |
| 7,402,811 B2 | 7/2008 | Hatanaka et al. |
| 7,443,296 B2 | 10/2008 | Mezhinsky et al. |
| 7,470,893 B2 * | 12/2008 | Suzuki et al. ............. 250/239 |
| 7,488,637 B2 | 2/2009 | Kim |
| 7,511,257 B2 | 3/2009 | Lee et al. |
| 7,517,351 B2 | 4/2009 | Culp et al. |
| 7,522,341 B2 | 4/2009 | Mouli |
| 7,525,168 B2 | 4/2009 | Hsieh |
| 7,534,645 B2 | 5/2009 | Choi |
| 7,535,037 B2 | 5/2009 | Lyu |
| 7,540,645 B2 | 6/2009 | Kazakevich |
| 7,542,069 B2 | 6/2009 | Tashiro |
| 7,544,163 B2 | 6/2009 | MacKinnon et al. |
| 7,545,434 B2 | 6/2009 | Bean et al. |
| 7,551,059 B2 | 6/2009 | Farrier |
| 7,564,935 B2 | 7/2009 | Suzuki |
| 7,567,291 B2 | 7/2009 | Bechtel et al. |
| 7,568,619 B2 | 8/2009 | Todd et al. |
| 7,573,516 B2 | 8/2009 | Krymski et al. |
| 7,578,786 B2 | 8/2009 | Boulais et al. |
| 7,583,872 B2 | 9/2009 | Seibel et al. |
| 7,589,349 B2 | 9/2009 | Hong |
| 7,595,210 B2 | 9/2009 | Shim |
| 7,598,686 B2 | 10/2009 | Lys et al. |
| 7,599,439 B2 | 10/2009 | Lavelle et al. |
| 7,605,016 B2 | 10/2009 | Min |
| 7,608,874 B2 | 10/2009 | Lee et al. |
| 7,612,318 B2 | 11/2009 | Jeon |
| 7,615,808 B2 | 11/2009 | Pain et al. |
| 7,615,838 B2 | 11/2009 | Kim |
| 7,616,986 B2 | 11/2009 | Seibel et al. |
| 7,630,008 B2 | 12/2009 | Sarwari |
| 7,646,407 B2 | 1/2010 | Fossum et al. |
| 7,663,115 B2 | 2/2010 | Korthout et al. |
| 7,744,528 B2 | 6/2010 | Wallace et al. |
| 7,749,799 B2 | 7/2010 | Pain |
| 7,768,562 B2 | 8/2010 | Boemler |
| 7,794,394 B2 | 9/2010 | Frangioni |
| 7,795,650 B2 | 9/2010 | Eminoglu et al. |
| 7,800,192 B2 | 9/2010 | Venezia et al. |
| 7,801,584 B2 | 9/2010 | Iddan et al. |
| 7,830,434 B2 | 11/2010 | Li et al. |
| 7,868,283 B2 | 1/2011 | Mabuchi |
| 7,871,373 B2 | 1/2011 | Yamada |
| 7,880,662 B2 | 2/2011 | Bogaerts |
| 7,901,974 B2 | 3/2011 | Venezia et al. |

(56) References Cited

U.S. PATENT DOCUMENTS

| | | |
|---|---|---|
| 7,914,447 B2 | 3/2011 | Kanai |
| 7,916,193 B2 | 3/2011 | Fossum |
| 7,923,763 B2 | 4/2011 | Lauxtermann |
| 7,935,050 B2 | 5/2011 | Launava et al. |
| 7,936,394 B2 | 5/2011 | Wu |
| 7,944,566 B2 | 5/2011 | Xie |
| 7,952,096 B2 | 5/2011 | Rhodes |
| 7,973,342 B2 | 7/2011 | Jeon |
| 7,995,123 B2 | 8/2011 | Lee et al. |
| 8,089,542 B2 | 1/2012 | Chevallier |
| 8,100,826 B2 | 1/2012 | MacKinnon et al. |
| 8,101,903 B2 | 1/2012 | Mokhnatyuk |
| 8,154,055 B2 | 4/2012 | Ha |
| 8,159,584 B2 | 4/2012 | Iwabuchi et al. |
| 8,193,542 B2 | 6/2012 | Machara |
| 8,212,884 B2 | 7/2012 | Seibel et al. |
| 8,300,111 B2 | 10/2012 | Iwane |
| 8,317,689 B1 | 11/2012 | Remijan et al. |
| 8,382,662 B2 | 2/2013 | Soper et al. |
| 8,384,814 B2 | 2/2013 | Chevallier |
| 8,396,535 B2 | 3/2013 | Wang et al. |
| 8,405,748 B2 | 3/2013 | Mao et al. |
| 8,423,110 B2 | 4/2013 | Barbato et al. |
| 8,471,938 B2 | 6/2013 | Altice, Jr. et al. |
| 8,476,575 B2 | 7/2013 | Mokhnatyuk |
| 8,493,474 B2 | 7/2013 | Richardson |
| 8,493,564 B2 | 7/2013 | Brukilacchio et al. |
| 8,523,367 B2 | 9/2013 | Ogura |
| 8,537,203 B2 | 9/2013 | Seibel et al. |
| 8,582,011 B2 | 11/2013 | Dosluoglu |
| 8,602,971 B2 | 12/2013 | Farr |
| 8,614,764 B2 | 12/2013 | Pitts et al. |
| 8,625,016 B2 | 1/2014 | Fossum et al. |
| 8,629,023 B2 | 1/2014 | Lee |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,675,125 B2 | 3/2014 | Cossairt et al. |
| 8,698,887 B2 | 4/2014 | Makino et al. |
| 8,733,660 B2 | 5/2014 | Wang et al. |
| 8,754,358 B2 | 6/2014 | Chou et al. |
| 8,797,434 B2 | 8/2014 | Lee et al. |
| 8,830,340 B2 | 9/2014 | Burt et al. |
| 8,836,834 B2 | 9/2014 | Hashimoto et al. |
| 8,854,517 B2 * | 10/2014 | Honda ............... H01L 27/14634 348/274 |
| 8,858,425 B2 | 10/2014 | Farr et al. |
| 8,885,034 B2 | 11/2014 | Adair et al. |
| 8,896,730 B2 | 11/2014 | Fossum |
| 8,952,312 B2 | 2/2015 | Blanquart et al. |
| 9,066,677 B2 | 6/2015 | Seto |
| 9,123,602 B2 | 9/2015 | Blanquart |
| 9,153,609 B2 | 10/2015 | Blanquart |
| 9,343,489 B2 | 5/2016 | Blanquart et al. |
| 2001/0030744 A1 | 10/2001 | Chang |
| 2001/0041825 A1 | 11/2001 | Shibata et al. |
| 2001/0052930 A1 | 12/2001 | Adair et al. |
| 2002/0011809 A1 | 1/2002 | Hartge et al. |
| 2002/0017611 A1 | 2/2002 | Tashiro et al. |
| 2002/0067408 A1 | 6/2002 | Adair et al. |
| 2002/0080248 A1 | 6/2002 | Adair et al. |
| 2002/0158986 A1 | 10/2002 | Baer |
| 2002/0163578 A1 | 11/2002 | Adair et al. |
| 2002/0180867 A1 | 12/2002 | Adair et al. |
| 2003/0007087 A1 | 1/2003 | Hakamata et al. |
| 2003/0052983 A1 | 3/2003 | Altree |
| 2003/0107664 A1 | 6/2003 | Suzuki |
| 2003/0163029 A1 | 8/2003 | Sonnenschein et al. |
| 2003/0187586 A1 | 10/2003 | Katzenmaier et al. |
| 2003/0189663 A1 | 10/2003 | Dolt et al. |
| 2003/0218120 A1 | 11/2003 | Shibayama |
| 2004/0036010 A1 | 2/2004 | Hsieh et al. |
| 2004/0049215 A1 | 3/2004 | Snow et al. |
| 2004/0078494 A1 | 4/2004 | Lennox et al. |
| 2004/0082833 A1 | 4/2004 | Adler et al. |
| 2004/0095495 A1 | 5/2004 | Inokuma et al. |
| 2004/0111012 A1 | 6/2004 | Whitman |
| 2004/0169771 A1 | 9/2004 | Washington et al. |
| 2004/0249267 A1 | 12/2004 | Gilboa |
| 2005/0027164 A1 | 2/2005 | Barbato et al. |
| 2005/0038322 A1 | 2/2005 | Banik |
| 2005/0075538 A1 | 4/2005 | Banik et al. |
| 2005/0131279 A1 | 6/2005 | Boulais et al. |
| 2005/0148819 A1 | 7/2005 | Noguchi et al. |
| 2005/0168941 A1 | 8/2005 | Sokol et al. |
| 2005/0174428 A1 | 8/2005 | Abe |
| 2005/0206755 A1 | 9/2005 | Yokoyama et al. |
| 2005/0222499 A1 | 10/2005 | Banik et al. |
| 2005/0231591 A1 | 10/2005 | Abe |
| 2005/0234302 A1 | 10/2005 | MacKinnon et al. |
| 2005/0288546 A1 | 12/2005 | Sonnenschein et al. |
| 2006/0007507 A1 | 1/2006 | Inaba et al. |
| 2006/0022234 A1 | 2/2006 | Adair et al. |
| 2006/0023109 A1 * | 2/2006 | Mabuchi ............... H01L 24/17 348/340 |
| 2006/0035415 A1 | 2/2006 | Wood et al. |
| 2006/0069314 A1 | 3/2006 | Farr |
| 2006/0164533 A1 | 7/2006 | Hsieh et al. |
| 2006/0181627 A1 | 8/2006 | Farrier |
| 2006/0221230 A1 | 10/2006 | Dutta et al. |
| 2006/0249765 A1 | 11/2006 | Hsieh |
| 2006/0250513 A1 | 11/2006 | Yamamoto et al. |
| 2006/0293563 A1 | 12/2006 | Banik et al. |
| 2006/0293565 A1 | 12/2006 | Uchimura et al. |
| 2007/0002134 A1 | 1/2007 | Ishihara et al. |
| 2007/0030345 A1 | 2/2007 | Amling et al. |
| 2007/0078328 A1 | 4/2007 | Ozaki et al. |
| 2007/0091190 A1 | 4/2007 | Iwabuchi et al. |
| 2007/0094303 A1 | 4/2007 | Zwingenberger et al. |
| 2007/0129601 A1 | 6/2007 | Johnston et al. |
| 2007/0138375 A1 | 6/2007 | Lee et al. |
| 2007/0153337 A1 | 7/2007 | Kim |
| 2007/0159526 A1 | 7/2007 | Abe |
| 2007/0182842 A1 | 8/2007 | Sonnenschein et al. |
| 2007/0185549 A1 | 8/2007 | Zdeblick |
| 2007/0187703 A1 | 8/2007 | Erchak |
| 2007/0197873 A1 | 8/2007 | Birnkrant |
| 2007/0225556 A1 | 9/2007 | Ortiz et al. |
| 2007/0244364 A1 | 10/2007 | Luanava et al. |
| 2007/0244365 A1 | 10/2007 | Wiklof |
| 2007/0276187 A1 | 11/2007 | Wiklof et al. |
| 2007/0297190 A1 | 12/2007 | Ng |
| 2008/0021271 A1 | 1/2008 | Pasero et al. |
| 2008/0042046 A1 | 2/2008 | Mabuchi |
| 2008/0045800 A2 | 2/2008 | Farr |
| 2008/0076967 A1 | 3/2008 | Couvillon, Jr. |
| 2008/0122031 A1 | 5/2008 | DeNatale et al. |
| 2008/0128740 A1 | 6/2008 | Yamashita et al. |
| 2008/0136319 A1 | 6/2008 | Yoon |
| 2008/0136945 A1 | 6/2008 | Blanquart et al. |
| 2008/0165360 A1 | 7/2008 | Johnston |
| 2008/0185314 A1 | 8/2008 | Tomasello et al. |
| 2008/0200758 A1 | 8/2008 | Orbay et al. |
| 2008/0208006 A1 | 8/2008 | Farr |
| 2008/0211634 A1 | 9/2008 | Hopkins et al. |
| 2008/0218609 A1 | 9/2008 | Blanquart et al. |
| 2008/0218615 A1 | 9/2008 | Huang et al. |
| 2008/0239070 A1 | 10/2008 | Westwick et al. |
| 2008/0249369 A1 | 10/2008 | Seibel et al. |
| 2008/0255416 A1 | 10/2008 | Gilboa |
| 2008/0258042 A1 * | 10/2008 | Krymski ............... H04N 3/155 250/208.1 |
| 2008/0287798 A1 | 11/2008 | Lee et al. |
| 2008/0309810 A1 | 12/2008 | Smith et al. |
| 2008/0316319 A1 | 12/2008 | Nomoto |
| 2009/0012361 A1 | 1/2009 | MacKinnon et al. |
| 2009/0012368 A1 | 1/2009 | Banik |
| 2009/0015301 A1 | 1/2009 | Marchesini et al. |
| 2009/0021628 A1 | 1/2009 | Tamakoshi |
| 2009/0040783 A1 | 2/2009 | Krupa et al. |
| 2009/0054908 A1 | 2/2009 | Zand et al. |
| 2009/0062656 A1 | 3/2009 | Hyuga |
| 2009/0074265 A1 | 3/2009 | Huang et al. |

(56) References Cited

U.S. PATENT DOCUMENTS

| | | |
|---|---|---|
| 2009/0076329 A1 | 3/2009 | Su et al. |
| 2009/0082630 A1 | 3/2009 | Tulley |
| 2009/0091641 A1 | 4/2009 | Hattori |
| 2009/0108176 A1 | 4/2009 | Blanquart |
| 2009/0141156 A1 | 6/2009 | Rossi et al. |
| 2009/0141180 A1 | 6/2009 | Kondo et al. |
| 2009/0154886 A1 | 6/2009 | Lewis et al. |
| 2009/0160976 A1 | 6/2009 | Chen et al. |
| 2009/0160979 A1 | 6/2009 | Xu et al. |
| 2009/0173974 A1 | 7/2009 | Shah et al. |
| 2009/0184349 A1 | 7/2009 | Dungan |
| 2009/0192390 A1 | 7/2009 | Berguer et al. |
| 2009/0200624 A1 | 8/2009 | Dai et al. |
| 2009/0203966 A1 | 8/2009 | Mizuyoshi |
| 2009/0208143 A1 | 8/2009 | Yoon et al. |
| 2009/0212397 A1 | 8/2009 | Tuttle |
| 2009/0216080 A1 | 8/2009 | Nakamura |
| 2009/0225548 A1 | 9/2009 | Narita |
| 2009/0230287 A1 | 9/2009 | Anderson et al. |
| 2009/0236500 A1 | 9/2009 | Shah et al. |
| 2009/0256905 A1 | 10/2009 | Tashiro |
| 2009/0265490 A1 | 10/2009 | Setya et al. |
| 2009/0268147 A1 | 10/2009 | Tang et al. |
| 2009/0278963 A1 | 11/2009 | Shah et al. |
| 2009/0292168 A1 | 11/2009 | Farr |
| 2009/0306478 A1 | 12/2009 | Mizuyoshi |
| 2009/0316116 A1 | 12/2009 | Melville et al. |
| 2009/0322911 A1 | 12/2009 | Blanquart |
| 2009/0322912 A1 | 12/2009 | Blanquart |
| 2010/0026824 A1 | 2/2010 | Chen |
| 2010/0039156 A1 | 2/2010 | Yamaguchi |
| 2010/0059802 A1 | 3/2010 | Chen |
| 2010/0118932 A1 | 5/2010 | Luo et al. |
| 2010/0121142 A1 | 5/2010 | OuYang et al. |
| 2010/0134662 A1 | 6/2010 | Bub |
| 2010/0137684 A1 | 6/2010 | Shibasaki et al. |
| 2010/0157037 A1 | 6/2010 | Iketani et al. |
| 2010/0157039 A1 | 6/2010 | Sugai |
| 2010/0178722 A1 | 7/2010 | de Graff et al. |
| 2010/0182446 A1 | 7/2010 | Matsubayashi |
| 2010/0198009 A1 | 8/2010 | Farr et al. |
| 2010/0204546 A1 | 8/2010 | Hassidov et al. |
| 2010/0228089 A1 | 9/2010 | Hoffman et al. |
| 2010/0276572 A1 | 11/2010 | Iwabuchi et al. |
| 2010/0290100 A1 | 11/2010 | Karasawa |
| 2010/0295978 A1* | 11/2010 | Nakamura ........ H01L 27/14609 348/273 |
| 2010/0305406 A1 | 12/2010 | Braun et al. |
| 2011/0028790 A1 | 2/2011 | Farr et al. |
| 2011/0034769 A1 | 2/2011 | Adair et al. |
| 2011/0034770 A1 | 2/2011 | Endo et al. |
| 2011/0037876 A1 | 2/2011 | Talbert et al. |
| 2011/0049591 A1 | 3/2011 | Nakatani et al. |
| 2011/0050874 A1 | 3/2011 | Reshef et al. |
| 2011/0055447 A1 | 3/2011 | Costa |
| 2011/0063428 A1 | 3/2011 | Sonnenschein et al. |
| 2011/0115663 A1 | 5/2011 | Bogaerts |
| 2011/0181840 A1 | 7/2011 | Cobb |
| 2011/0208004 A1 | 8/2011 | Feingold et al. |
| 2011/0237882 A1 | 9/2011 | Saito |
| 2011/0237884 A1 | 9/2011 | Saito |
| 2011/0238977 A1 | 9/2011 | Talbert et al. |
| 2011/0245605 A1 | 10/2011 | Jacobsen et al. |
| 2011/0263941 A1 | 10/2011 | Wright et al. |
| 2011/0288374 A1 | 11/2011 | Hadani et al. |
| 2011/0295061 A1 | 12/2011 | Haramaty et al. |
| 2012/0004508 A1 | 1/2012 | McDowall et al. |
| 2012/0029279 A1 | 2/2012 | Kucklick |
| 2012/0035419 A1 | 2/2012 | Ashida et al. |
| 2012/0035434 A1 | 2/2012 | Ferren et al. |
| 2012/0041267 A1 | 2/2012 | Benning et al. |
| 2012/0041534 A1 | 2/2012 | Clerc et al. |
| 2012/0050592 A1 | 3/2012 | Oguma |
| 2012/0078052 A1 | 3/2012 | Cheng |
| 2012/0113506 A1 | 5/2012 | Gmitro et al. |
| 2012/0120282 A1 | 5/2012 | Goris |
| 2012/0140302 A1 | 6/2012 | Xie et al. |
| 2012/0147229 A1 | 6/2012 | Shah et al. |
| 2012/0265196 A1 | 10/2012 | Turner et al. |
| 2012/0293699 A1 | 11/2012 | Blanquart et al. |
| 2012/0307030 A1 | 12/2012 | Blanquart |
| 2013/0010166 A1 | 1/2013 | Morisaki et al. |
| 2013/0126707 A1 | 5/2013 | Blanquart |
| 2013/0126708 A1 | 5/2013 | Blanquart |
| 2013/0144122 A1 | 6/2013 | Adair et al. |
| 2013/0158346 A1 | 6/2013 | Soper et al. |
| 2013/0176409 A1 | 7/2013 | Kotani et al. |
| 2013/0222165 A1 | 8/2013 | David et al. |
| 2013/0242069 A1 | 9/2013 | Kobayashi |
| 2013/0292854 A1 | 11/2013 | Lua et al. |
| 2013/0300837 A1 | 11/2013 | DiCarlo et al. |
| 2014/0052004 A1 | 2/2014 | D'Alfonso et al. |
| 2014/0073852 A1 | 3/2014 | Banik et al. |
| 2014/0104466 A1 | 4/2014 | Fossum |
| 2014/0160259 A1 | 6/2014 | Blanquart et al. |
| 2014/0175591 A1 | 6/2014 | Tian et al. |
| 2014/0198240 A1 | 7/2014 | Rhoads |
| 2014/0203084 A1 | 7/2014 | Wang |
| 2014/0217268 A1 | 8/2014 | Schleipen et al. |
| 2014/0267851 A1 | 9/2014 | Rhoads |
| 2014/0300698 A1 | 10/2014 | Wany |
| 2014/0354788 A1 | 12/2014 | Yano |
| 2014/0364689 A1 | 12/2014 | Adair et al. |
| 2016/0155765 A1 | 6/2016 | Blanquart |
| 2016/0190197 A1 | 6/2016 | Blanquart |

FOREIGN PATENT DOCUMENTS

| | | |
|---|---|---|
| CN | 100407433 C | 7/2008 |
| CN | 101214154 A | 7/2008 |
| CN | 100502024 C | 6/2009 |
| CN | 101640211 A | 2/2010 |
| CN | 101715644 A | 5/2010 |
| CN | 101848344 A | 9/2010 |
| CN | 101978598 A | 2/2011 |
| CN | 103636000 A | 3/2014 |
| CN | 103650476 A | 3/2014 |
| EP | 1618833 A1 | 1/2006 |
| EP | 1628348 A1 | 2/2006 |
| EP | 2108305 A1 | 10/2009 |
| EP | 2234387 A1 | 9/2010 |
| EP | 2302905 A1 | 3/2011 |
| EP | 2442558 A1 | 4/2012 |
| IL | 229396 | 7/2016 |
| IL | 229397 | 7/2016 |
| JP | 2001339057 | 7/2001 |
| JP | 2002-329851 | 11/2002 |
| JP | 2006-025852 | 2/2006 |
| JP | 2006-049361 | 2/2006 |
| JP | 2007-228460 | 9/2007 |
| JP | 2008-235478 | 10/2008 |
| JP | 2008-290817 | 12/2008 |
| JP | 2009206958 A | 9/2009 |
| JP | 2010-252396 | 11/2010 |
| JP | 2010-273757 | 12/2010 |
| WO | 9413191 | 6/1994 |
| WO | 9605693 A1 | 2/1996 |
| WO | 0108549 A1 | 2/2001 |
| WO | 2004093438 | 10/2004 |
| WO | 2006080015 A2 | 8/2006 |
| WO | 2006129762 A1 | 12/2006 |
| WO | 2009135255 | 11/2009 |
| WO | 2012155142 A1 | 11/2012 |
| WO | 2012155143 A1 | 11/2012 |
| WO | 2012155150 A1 | 11/2012 |
| WO | 2012155152 A1 | 11/2012 |
| WO | 2014018948 A2 | 1/2014 |
| WO | 2014145246 A1 | 9/2014 |
| WO | 2014145248 A1 | 9/2014 |
| WO | 2014275783 A1 | 9/2014 |
| WO | 2014285645 A1 | 9/2014 |
| WO | 2015215560 A1 | 7/2015 |

* cited by examiner

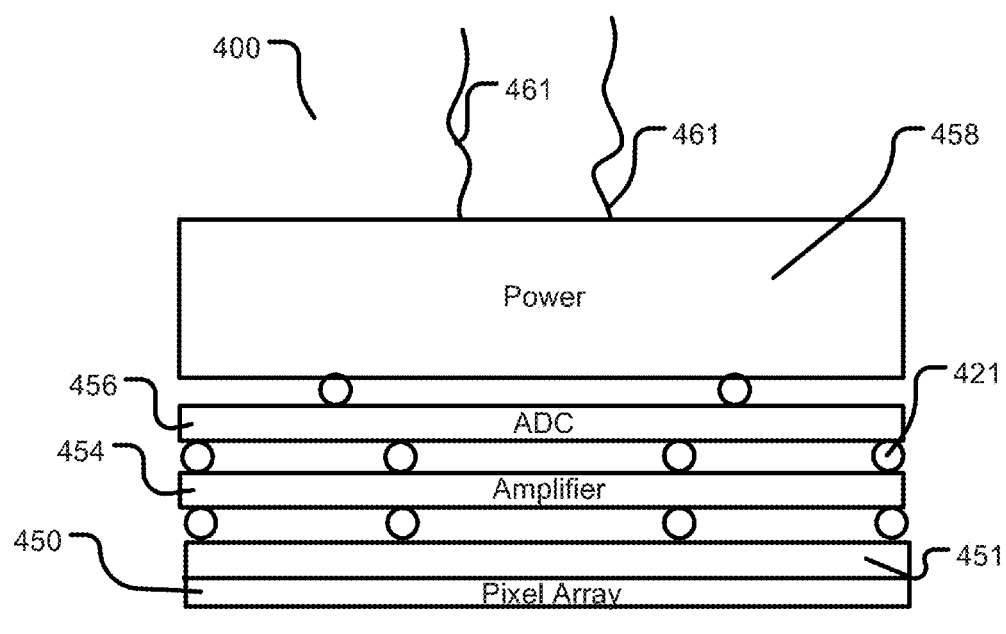
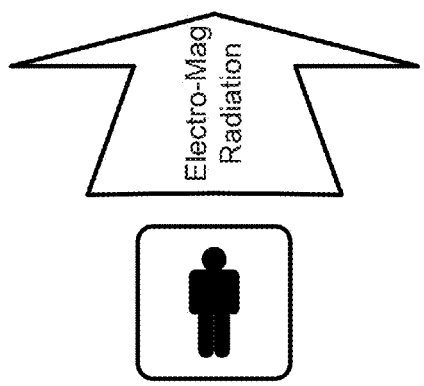
FIG. 1

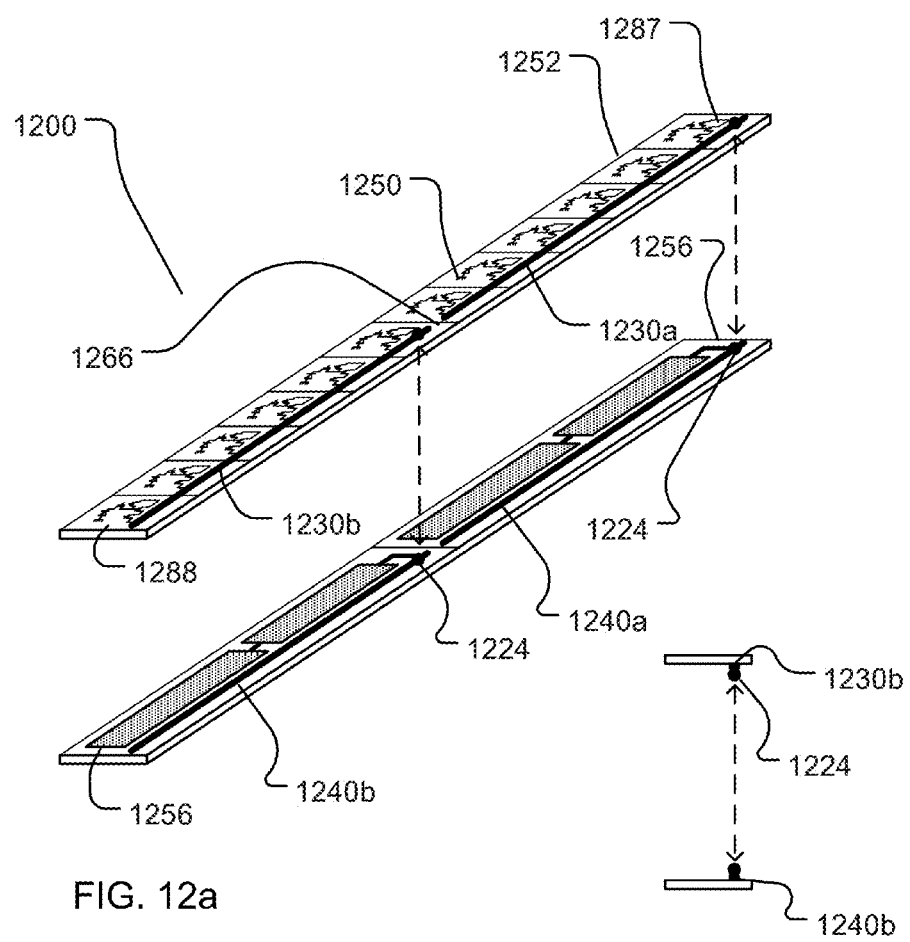
FIG. 12a
FIG. 12b
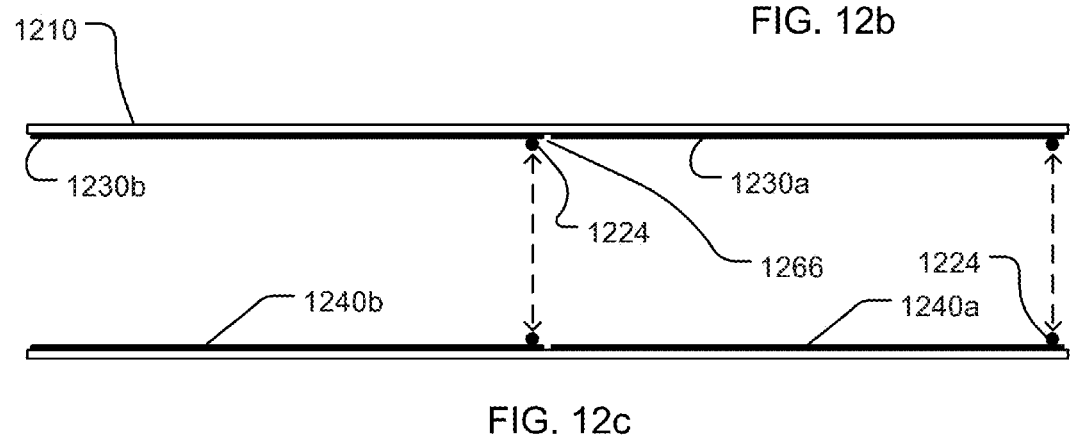
FIG. 12c

SYSTEM AND METHOD FOR SUB-COLUMN PARALLEL DIGITIZERS FOR HYBRID STACKED IMAGE SENSOR USING VERTICAL INTERCONNECTS

CROSS-REFERENCE TO RELATED APPLICATIONS

This application claims the benefit of: (1) U.S. Provisional Application No. 61/485,426, filed May 12, 2011; (2) U.S. Provisional Application No. 61/485,432, filed May 12, 2011; (3) U.S. Provisional Application No. 61/485,435, filed May 12, 2011; and, (4) U.S. Provisional Application No. 61/485,440, filed May 12, 2011, which are all hereby incorporated by reference herein in their entireties, including but not limited to those portions that specifically appear hereinafter, the incorporation by reference being made with the following exception: In the event that any portion of the above-referenced provisional applications are inconsistent with this application, this application supersedes said above-referenced provisional applications.

STATEMENT REGARDING FEDERALLY SPONSORED RESEARCH OR DEVELOPMENT

Not Applicable.

BACKGROUND

The disclosure relates generally to electromagnetic sensing and sensors and also relates to low energy electromagnetic input conditions as well as low energy electromagnetic throughput conditions. The disclosure relates more particularly, but not necessarily entirely, to optimizing the pixel array area and using a stacking scheme for a hybrid image sensor with minimal vertical interconnects between substrates and associated systems, methods and features, which may also include maximizing pixel array size/die size (area optimization).

There has been a popularization of the number of electronic devices that utilize and include the use of imaging/camera technology in general. For example, smartphones, tablet computers, and other handheld computing devices all include and utilize imaging/camera technology. The use of imaging/camera technology is not limited to the consumer electronics industry. Various other fields of use also utilize imaging/camera technology, including various industrial applications, medical applications, home and business security/surveillance applications, and many more. In fact, imaging/camera technology is utilized in nearly all industries.

Due to such popularization, the demand for smaller and smaller high definition imaging sensors has increased dramatically in the marketplace. The device, system and methods of the disclosure may be utilized in any imaging application where size and form factor are considerations. Several different types of imaging sensors may be utilized by the disclosure, such as a charged-couple device (CCD), or a complementary metal-oxide semiconductor (CMOS), or any other image sensor currently known or that may become known in the future.

CMOS image sensors typically mount the entire pixel array and related circuitry, such as analog-digital converters and/or amplifiers, on a single chip. Because of the physical constraints of the chip size itself and the physical space occupied by related circuitry involved in a conventional CMOS image sensor, the area that the pixel array may occupy on the chip is often limited. Thus, even if the pixel array were maximized on a substrate that also contains the related circuitry, the pixel array is physically limited in area due to the amount of physical area and space that the related circuitry for signal processing and other functions occupies on the chip.

Further, the application or field of use in which the CMOS image sensor may be used often requires the CMOS image sensor to be limited to a certain size also limiting the physical area in which the pixel array may occupy. The size limitations of a CMOS image sensor often require trade-offs between image quality and other important functions, such as signal processing, due to the number of considerations that must be accounted for in the design and manufacture of a CMOS image sensor. Thus, for example, increasing the pixel array area may come with a trade-off in other areas, such as A/D conversion or other signal processing functions, because of the decreased area in which the related circuitry may occupy.

The disclosure optimizes and maximizes the pixel array without sacrificing quality of the signal processing by optimizing and maximizing the pixel array on a first substrate and stacking related circuitry on subsequent substrates. The disclosure utilizes advancements in back-side illumination and other areas to take advantage of optimizing the area of the pixel array on a substrate. The stacking scheme and structure allow highly functional, large-scale circuits to be utilized while maintaining a small chip size.

The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 1 illustrates an embodiment of an imaging sensor built on a plurality of substrates and also illustrating an embodiment of the specific placement of support circuits in accordance with the teachings and principles of the disclosure;

FIGS. 12a-12c illustrate perspective, front and side views, respectively, of a single column of pixels that have been formed into two separate sub-columns of pixels, wherein each pixel sub-column is attached to a different pixel column read bus, and illustrating two columns of circuitry taken from FIG. 12 showing an electrical connection therebetween;

DETAILED DESCRIPTION

Figure 2:
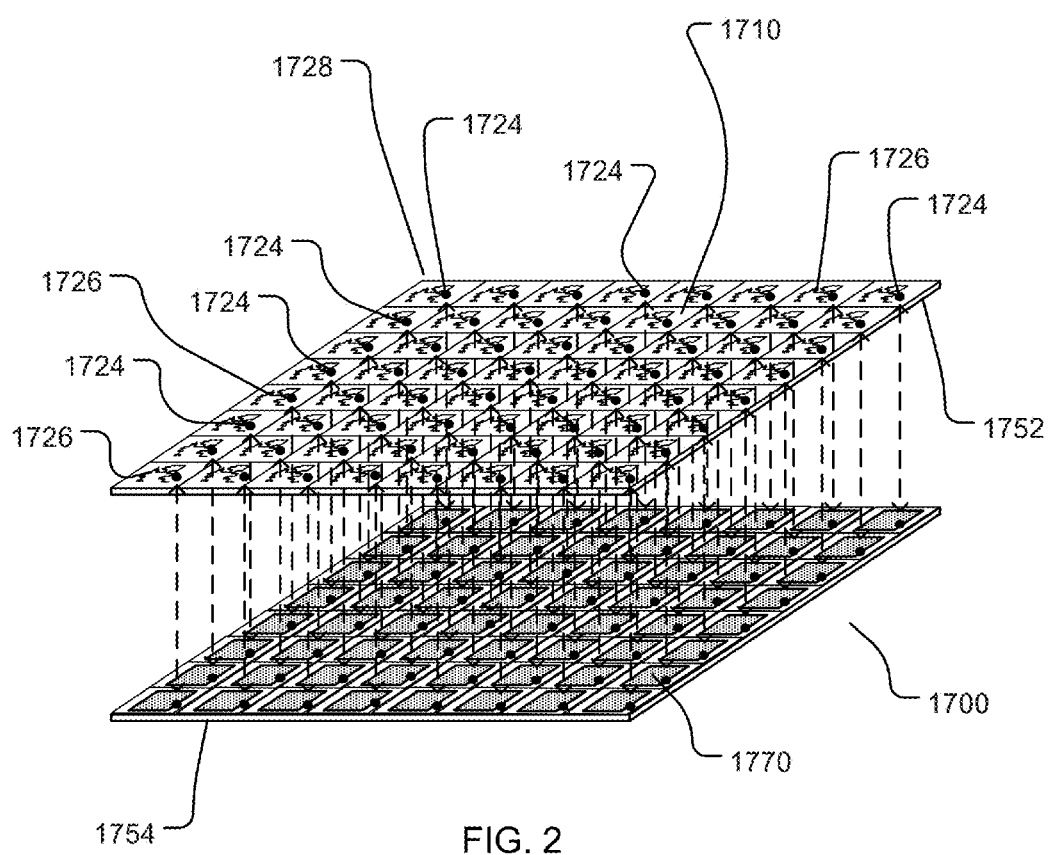
FIG. 2 illustrates an embodiment of a pixel array wherein interconnects are spaced relative to pixels within the pixel array in accordance with the teachings and principles of the disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the devices, systems, methods and processes for staggering ADC or column circuit bumps in a column or sub-column hybrid image sensor using vertical interconnects are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

It must be noted that, as used in this specification and the appended claims, the singular forms "a," "an," and "the" include plural referents unless the context clearly dictates otherwise.

In describing and claiming the subject matter of the disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

Digital imaging, whether still or movie, has many constraints placed upon it with regard to the devices used to record the image data. As discussed herein, an imaging sensor may include a pixel array and supporting circuits that are disposed on at least one substrate. Devices usually have practical and optimal constraints on the form factor of the imaging sensor depending upon the application. Often it is not the pixel array that is the only consideration for fitment, but it is the supporting circuitry that needs to be accommodated. The supporting circuits may be, but are not necessarily limited to, analog to digital converters, power circuits, power harvesters, amplifier circuits, dedicated signal processors and filters, serializers for transmission preparation, etc. In addition to circuits, physical property elements may be required, such as light filters and lenses. Each of the pixels must be read from the pixel array and have the data processed by the supporting circuits. With the increase in the number of pixels in an array, more data must be handled. In regard to movie data the sensor must dump its data and be ready to operate again in short order.

Although size is an issue as stated above, pixel count numbers continue to climb industry wide no matter the specific application, and often eclipse the mediums that are used to actually view the images after they have been recorded, such as a computer monitor or television. However, it should be understood that all pixels are not created equal. In the example above, a scope configuration may be used in a limited light application.

As pixel counts continue to grow in a given space pixel pitch decreases thereby requiring greater precision for interconnect electrical contact. Accordingly, the cost of image sensor production can increase as the need for greater precision in data handling is required for the increased pixel pitch. Current technologies may be used to achieve image sensors with increased capabilities but at increased cost as yields fall during manufacture.

The above-identified issues describe the current state of the art relative to a few needs within the industry. What is needed is an image sensor having adequate resolution by way of pixel count, a vertical architecture and form factor, and as large as possible pixel size, all while constrained in a limited space. The disclosure contemplates and will discuss embodiments and methods of design that address these and potentially other issues by optimizing the size of the pixel array on a substrate/chip and remotely locating supporting circuits in a generally vertical configuration on one or more supporting substrates/chips.

High performance image sensors that use on-chip analog to digital convertors (ADC), on-chip digital and analog algorithms, on-chip complex timings, and on-chip complex analog functions provide high quality images because of the following reasons (the list below is not a complete list, but is given merely for exemplary purposes):

No pick-up noise due to long off-chip analog data lines (if no on-chip ADC, then analog signals need to be sent off-chip);

Lower temporal noise because digital conversion is carried out early in the data path (no extra amplifier, buffer that will add extra noise);

Local timing optimization using complex on-chip timing generator. Because of pad count limitation, only simple timing can be performed using external system;

Lower noise generated by I/O. On-chip systems allow for reduced pad count; and

Faster operation can be achieved (more serial on-chip operation, reduced stray capacitances and resistances). With larger and larger arrays, the need to read and processes the data created therein is paramount.

The disclosure also contemplates an image sensor that might otherwise be manufactured with its pixel array and supporting circuitry on a single, monolithic substrate/chip and separating the pixel array from all or a majority of the supporting circuitry. The disclosure may use at least two substrates/chips, which will be stacked together using three-dimensional stacking technology. The first of the two substrates/chips may be processed using an image CMOS process. The first substrate/chip may be comprised either of a pixel array exclusively or a pixel array surrounded by limited circuitry. The second or subsequent substrate/chip may be processed using any process, and does not have to be from an image CMOS process. The second substrate/chip may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip may be stacked with the second or subsequent substrate/chip using any three-dimensional technique. The second substrate/chip may support most, or a majority, of the circuitry that would have otherwise been implemented in the first image CMOS chip (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wirebonds, μbump and/or TSV (Through Silicon Via).

Referring now to FIG. 1, an embodiment of an image sensor with its pixel array and supporting circuitry built on a plurality of substrates is illustrated using backside illumination. As can be seen in the figure, a pixel array 450 may be disposed on a first substrate 452. The first substrate 452 may be made of silicon or of another material in order to control light transmission characteristics. Solder balls, bumps or vias 421 may be used to electrically connect one substrate to another. An embodiment of a stacked image sensor may comprise a pixel array 450 on a first substrate 452. The pixel array 450 may cover at least forty percent of a first surface 451 of the first substrate 452. In a backside illuminated configuration, a pixel array may be disposed on the backside of said first substrate. Further, in a back side illumination configuration the substrate 452 may be thinned for controlling light transmission therethough. In an embodiment utilizing backside illumination, the first substrate may be made of primarily silicon material, or the first substrate may be made of primarily of "High-Z" semiconductor material (Cadmium Telluride e.g.), or the first substrate may be made primarily of III-V semiconductor materials (Gallium Arsenide e.g.).

In an embodiment, a pixel array 450 may cover a majority of the first surface 451 of a first substrate 452. In such an embodiment the pixel array 450 may be situated or located on any portion of said first surface 451. The remaining space on the first surface 451 may be used for secondary circuit placement if desired. Situations may arise where a secondary circuit may be sized such that central placement of the pixel array is not practical.

Figure 3:
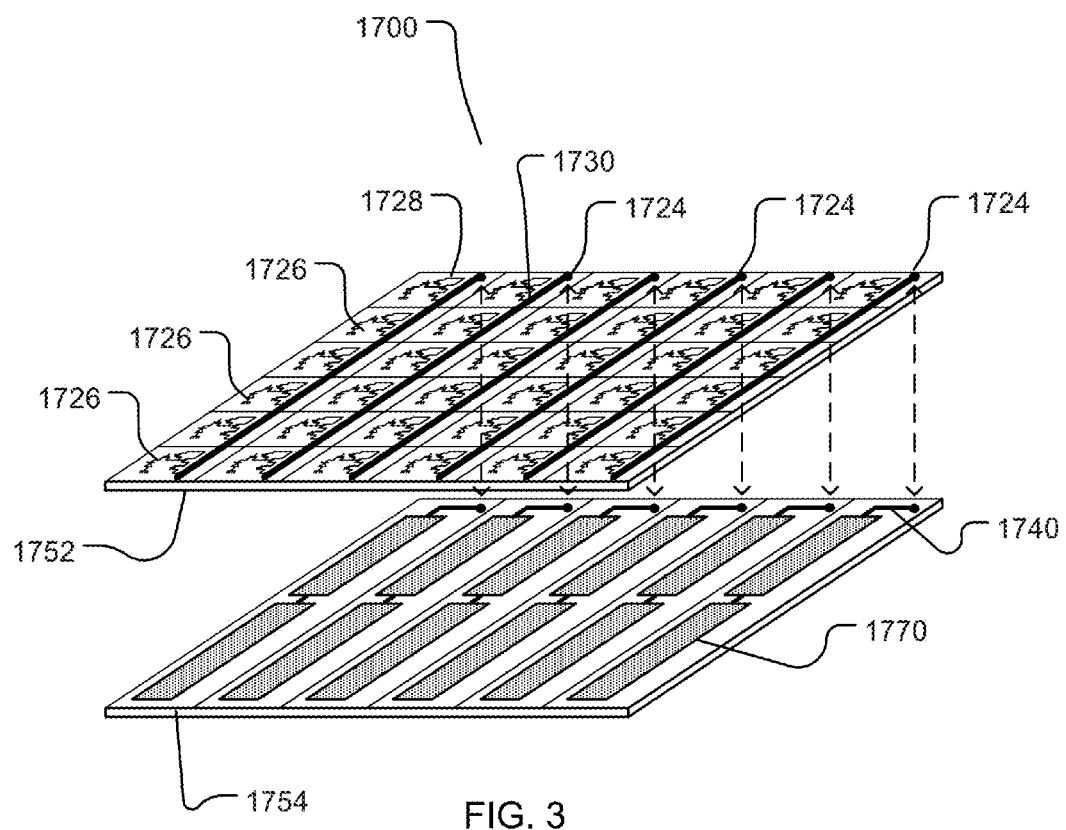
FIG. 3 illustrates an embodiment of a pixel array wherein interconnects are spaced relative to columns within the pixel array in accordance with the teachings and principles of the disclosure.

During use, data created by individual pixels on the pixel array must be processed by supporting circuitry, as such each pixel must be electronically connected to supporting circuits. Ideally each pixel could be read simultaneously thereby creating a global shutter. Referring now to FIG. 2, it will be appreciated that the ability to read data from an imaging device as a global shutter requires that there be one interconnect 1724 per pixel 1726, which is very difficult to achieve in practice because of the bumping pitch during manufacturing tolerances. FIG. 3 illustrates a situation where the pixels 1726 have been formed in a plurality of columns, such as 1728. Using a pixel column (1728) format in a pixel array, a very high frame rate can be achieved by using a rolling type shutter. It will be appreciated that a rolling type shutter reads an entire row of pixels substantially simultaneously at one time and then reads or moves from the top of the pixel columns to ° the bottom of the pixel columns. In other words, the first row of pixels may be read followed by the next, adjacent row of pixels as data is read from the plurality of pixel columns, and the reading starts at the top of the pixel columns and then rolls down the columns, pixel by pixel at a time, and moves in a predetermined and calculated pattern over the entirety of the pixel array. In the case of a rolling shutter, only one read bus 1730 need be present per pixel column 1728, and one read bus 1740 per circuit column. Due to the superimposition of the read buses 1730 and 1740 on the first substrate 1752 and the second substrate 1754, respectively, only one interconnect/bump 1724 per pixel column bus 1730 is required to connect the pixel read bus 1730 to the circuit read bus 1740, instead of one interconnect/bump 1724 per pixel 1726 as required by a global shutter.

FIG. 2 illustrates a bumping configuration or scheme using one bump 1724 per pixel 1726, which approximates a global shutter operation. In this configuration, the bump pitch equals or substantially equals the pixel pitch in both the X and Y axes or directions. FIG. 3 illustrates a bumping configuration or scheme using one interconnect/bump 1724 per pixel column 1728. This configuration may be used in a rolling shutter operation. This bump pitch configuration or scheme is more relaxed as compared to the bump pitch of FIG. 2 in the vertical direction only. However, it should be noted that in this configuration the bump pitch is still required to be at least the same in one direction or dimension as the pixel pitch. FIG. 3 illustrates a plurality of columns 1728, where each column 1728 is comprised of a plurality of pixels 1726. Each column of pixels may run in the Y direction (y-axis) for a distance and may be one pixel in width as illustrated. Each column of pixels may be read through a single connection point at one end of each column 1728. Although such a configuration simplifies chip architecture, tight tolerances must still be maintained because the distance between pixels laterally (horizontally) continues to limit bump (interconnect) pitch because the interconnect must not make contact with a neighboring interconnect and must be sized accordingly.

Figure 4:
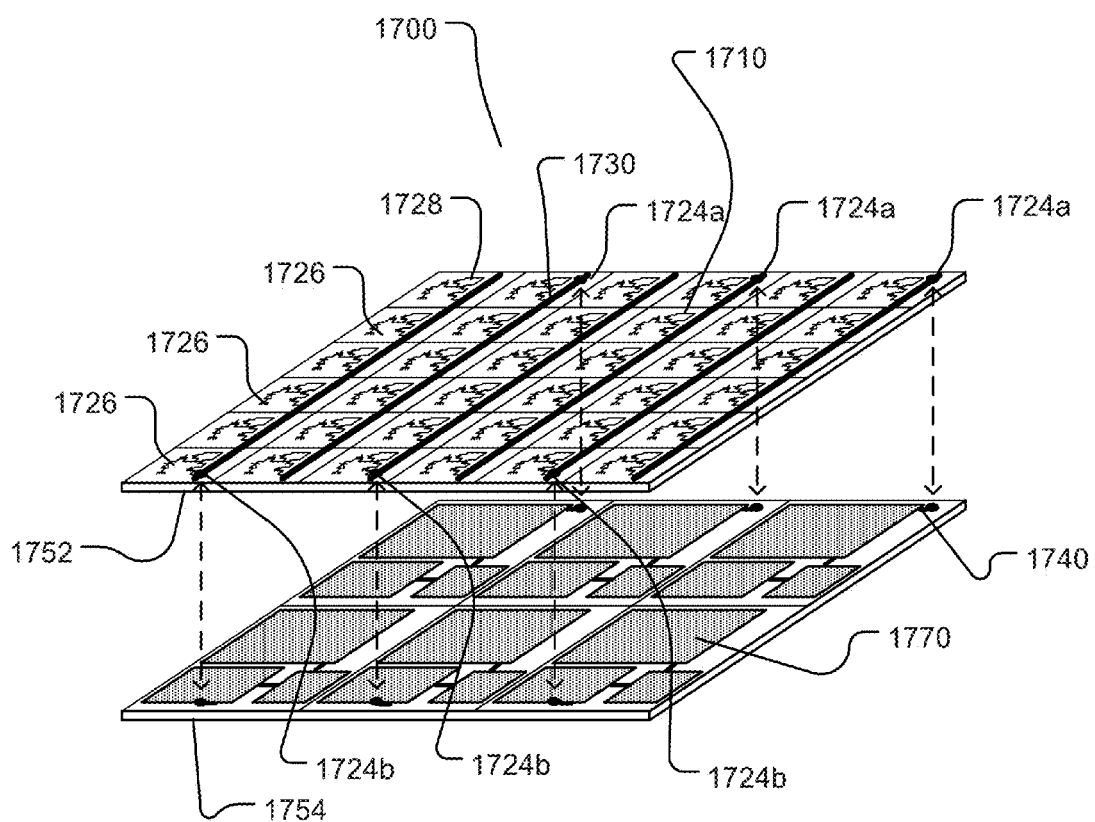
FIG. 4 illustrates an embodiment of a pixel array wherein a interconnects are spaced relative to areas within the pixel array in accordance with the teachings and principles of the disclosure.

FIG. 4, illustrates a bumping configuration that is even further relaxed than that shown in FIG. 2 or 3. In this figure, the bump pitch is relaxed (e.g., the distance between bumps has increased in comparison to FIGS. 2 and 3) and half of the interconnects/bumps 1724 can be used to process data at each side of the pixel array 1710. This can be accomplished by adding or introducing a second set of interconnects 1724 that alternate with respect column read buses and at opposing ends of the column read buses (e.g., an interconnect 1724 is used to connect read buses 1730, 1740 and may be located at every other column read bus on one side of the pixel array 710 and the opposite may be done on the other side of the pixel array 710). As can be seen in FIG. 4, the second set of interconnects 1724b may be used in combination with the first set of interconnects 1724a and may be employed to allow half of the data to be processed or read at each side of the pixel array 1710. Such a configuration may allow for nearly double the size of bump pitch (interconnect pitch) as compared to the pixel pitch in at least one dimension, which would greatly decrease the cost of producing image sensors 1700. In an embodiment, more than one interconnect or bump 1724 per pixel column 1728 may be utilized per read bus, such that data may be read from either end of the pixel column 1728.

FIGS. 5-10 illustrate embodiments and configurations of a pixel array 1810 having staggered interconnect or bump 1824 positioning on a substrate/chip. As noted above, because there is one read bus 1830 per pixel column 1828, 1832 and one read bus 1840 per circuit column, and because the read buses 1830 and 1840 run from the top of the column to the bottom of the column, the interconnect/bump 1824 may be placed anywhere along the superimposed path of the buses within the column. In order to relax the bumping pitch, the bump distance may be increased from column to column by shifting the next column bump 1824 either up or down (in the Y direction) in the next column.

By way of example, it will be appreciated that pixel pitch may be about 5 μm and pixel column may be any length, for example between about 2 mm and about 15 mm long. It should be noted that bump pitch is a function of pixel pitch, such that the pixel pitch will be determinative of an ideal bump pitch. For example, assuming there is a desired bump pitch of approximately 100 μm, placing a first interconnect or bump 1824 may then be accomplished by starting at the top of the first column and shifting down the next column interconnect or bump by 100 μm. All other bumps are similarly positioned until the interconnect or bump in the 20th column of the line will be located at the bottom of the pixel column. At that point, the interconnect or bump 1824 in the 21st column may again be placed at the top of the pixel column 1828. This same pattern may then be repeated until the end of the pixel array 1810. Horizontally, the interconnects or bumps 1824 may be separated by 20 columns×5 μm=100 μm). In this example, all bumps will then be separated by more than 100 μm, even though the pixel pitch is about 5 μm. Redundancy can then be introduced in the pixel column for yield purposes. For example, bumps in all columns can be doubled (i.e., the two read buses are attached by 2 interconnects or bumps). This technique would significantly increase stacking yield and lower the cost of the overall process.

Figure 5:
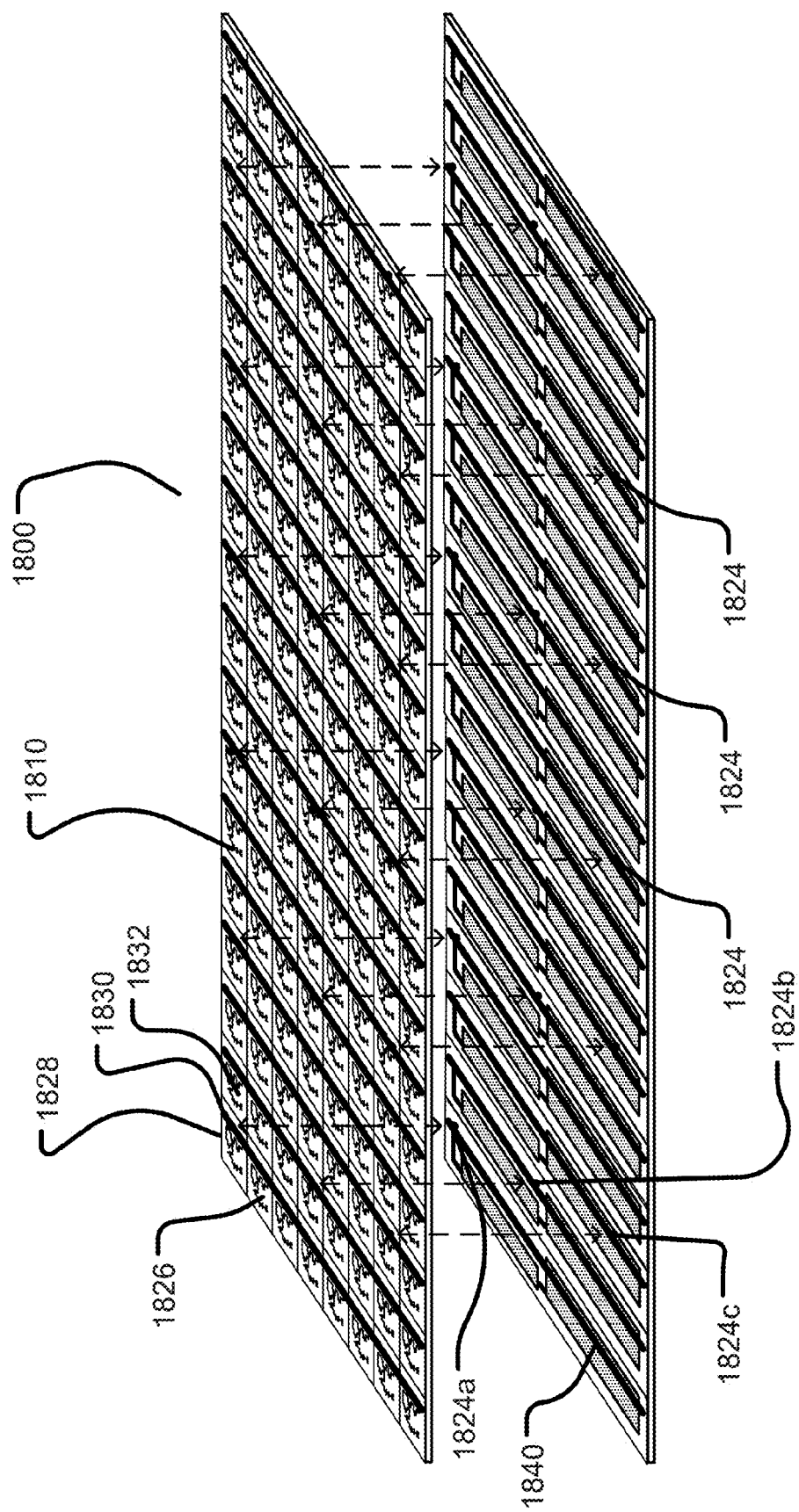
FIG. 5 illustrates a perspective view of an embodiment of an imaging sensor built on a plurality of substrates wherein a plurality of pixel columns forming the pixel array are located on the first substrate and a plurality of circuit columns are located on a second substrate and showing an electrical connection and communication between one column of pixels to its associated or corresponding column of circuitry via interconnects, wherein interconnects may be spaced relative to defined pixel areas within the pixel array in accordance with the teachings and principles of the disclosure.

As can be seen in FIG. 5, a first column 1828 of pixels 1826 may be electrically accessed via a first interconnect 1824a. In the embodiment, a second pixel column 1832 may be electrically accessed through a second interconnect 1824b, which has been positioned during manufacture in a staggered configuration relative to said first interconnect 1824a. As illustrated, the location or position of the second interconnect 1824b may be at least two pixel widths away from the position of the first interconnect 1824b (and from any other interconnect 1824) in both the X and Y dimensions or directions. A third interconnect 1824c may then be positioned in like manner in a third pixel column and so on for N-number of interconnects 1824 across the pixel array 1810. Such a configuration provides for an interconnect pitch that is at least three times that of the pixel pitch. It will be appreciated that the gain in interconnect pitch may be much greater than three times that of the pixel pitch under standard conditions. However, it will be appreciated that the gain in interconnect pitch may be at least three times the pixel pitch as noted above.

Likewise, greater interconnect gains may be made with area based spacing rather than column-by-column based connectivity (see figures illustrating a pixel column aspect ratio of 6/1 and circuit column aspect ratio of 6/1 and 3/2, or a pixel column aspect ratio of 8/1 and circuit column aspect ratio of 2/4). This can be accomplished with the addition of more bus structures or use of direct reading to a subsequent substrate. In either configuration, the interconnect pitch may be described thusly:

$$\text{Interconnect\_Pitch} = \sqrt{(N^*\text{PixelPitch}_x)^2 + (M^*\text{PixelPitch}_y)^2}$$

where N is the number of pixels between two adjacent interconnects in the X-direction and M is the number of pixels between two adjacent interconnects in the Y-direction. It will be appreciated that each of the plurality of interconnects may be a bump where the bump to bump distance may be greater than two pixels in width, or greater than four pixels in width, or greater than eight pixels in width.

Figure 6:
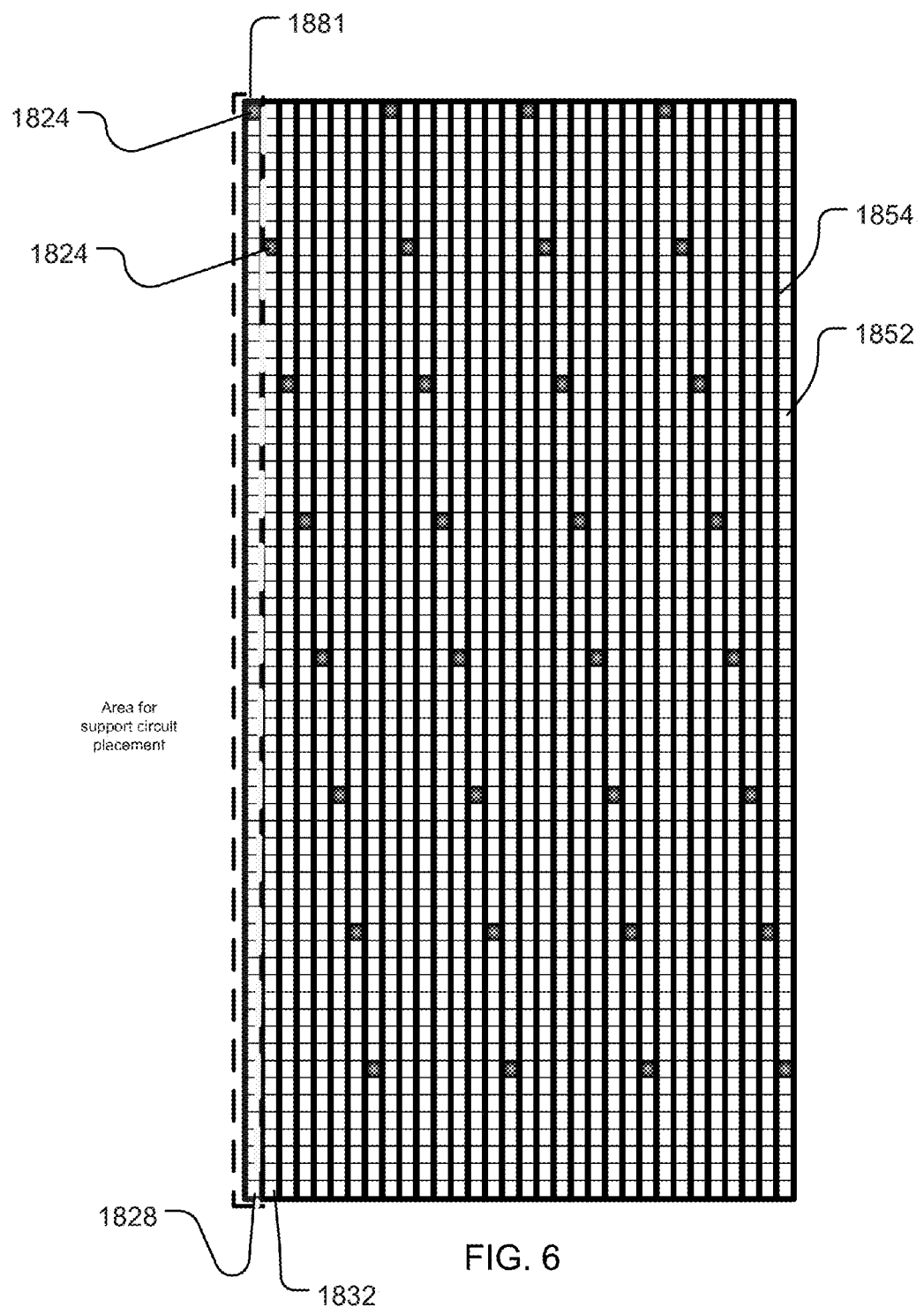
FIGS. 6-10 illustrate top views of various embodiments of an imaging sensor built on a plurality of substrates wherein a plurality of pixel columns forming the pixel array are located on the first substrate and a plurality of circuit columns are located on a second substrate and showing an electrical connection and communication between one column of pixels to its associated or corresponding column of circuitry via interconnects, wherein interconnects may be spaced relative to defined pixel areas within the pixel array in accordance with the teachings and principles of the disclosure.

In many applications, the N×Pixel Pitch in the X direction will be equal to M×Pixel Pitch in the Y direction. As illustrated in FIGS. 6-10, larger pixel arrays 1810 may be accommodated or designed by extrapolating the above described process through additional iterations. FIG. 6 illustrates a superimposed silicon substrate stack. In the figure, a first substrate 1852 consisting of a pixel array 1810 is shown overlaid on top of a support substrate 1854 that comprises support circuits. The area available for locating support circuits for a first pixel column 1881 is outlined in dashed lines and labeled for the sake of simplicity and discussion. It will be appreciated that the actual area of the circuit column is not represented by the dashed lines, but may be greater than, less than or the same as the area of the pixel column. As discussed above, the support circuit area directly correlates to the area of a pixel column to which they correspond. Each pixel column may be one pixel wide and sixty-four pixels long and may have one read bus that runs from the top to the bottom of the pixel column. In FIG. 6, the area available for support circuit placement may be equal to one pixel unit wide by sixty-four pixel units long, which is shown as the heavier vertical lines in the figure. Therefore, the interconnect 1824 between the substrates in FIG. 6 must fall somewhere within the sixty-four pixel unit area in order to read that column, since the pixel column read bus and the column circuit read bus are superimposed along the path of the sixty-four pixels, such that the interconnect 1824 may be placed anywhere along those sixty-four pixels to connect the read buses.

Moreover, because the interconnect can be located only where the pixel column read bus and the support circuit read bus superimpose, the interconnect range in order to read the corresponding pixel column is 1 pixel wide and 64 pixels long (for this example), which is the intercept between the pixel column and the support circuit to be connected.

It should be noted that the exemplary aspect ratio of the support circuit area in FIG. 6 is illustrated as 1/64. There are many options to locate or place the interconnect 1824 within that area and the ultimate location may then be chosen by the designer so as to allow the desired spacing from interconnect to interconnect. For example, as illustrated best in FIGS. 6-10, it will be appreciated that in an embodiment in which the interconnects or bumps 1824 are in a staggered configuration, there may be one interconnect or bump 1824 per group of pixels 1826.

Additionally, it should be noted that various read bus architectures may be utilized depending on the desired application. As discussed above, larger dedicated support circuits may be employed to process the data read through each interconnect 1824. The staggering of the position of each interconnect/bump 1824 may also provide even greater space for support circuits relative to each area or group of pixels within the pixel array 1810.

It should also be noted that many optimum staggering configurations have been found for the same base sensor with different support circuit aspect ratios as illustrated in FIGS. 6-10. An optimum configuration can be found by varying the position of the interconnect within the range of the intercept between the pixel column and the support circuit and the pattern of the allocation of the support circuit to each pixel column. It should also be noted that, all interconnects illustrated in FIGS. 6-10 are more than 7 pixels in distance away from each other.

Figure 7:
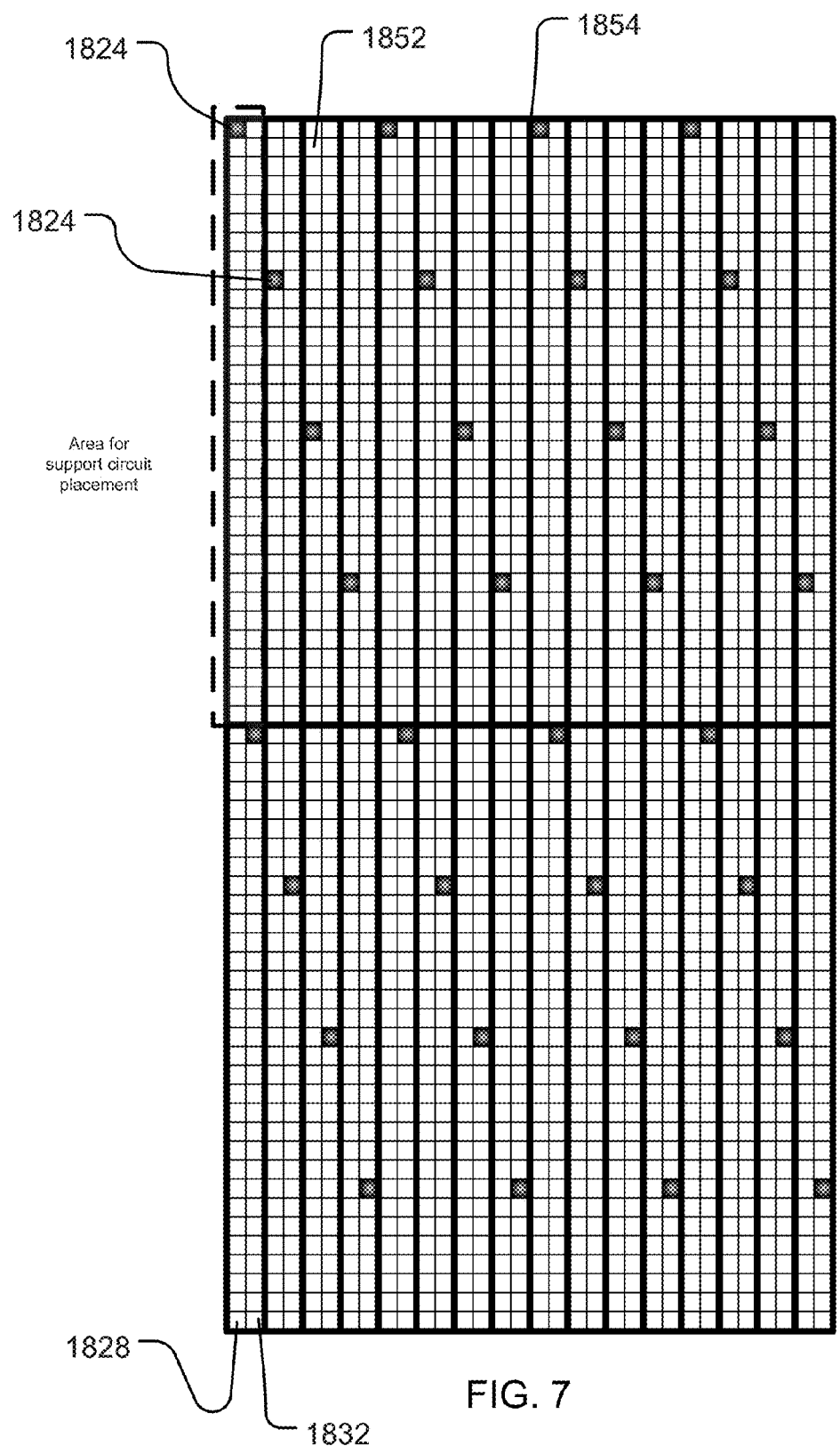

In FIG. 7, the area available for support circuit placement may be equal to two pixel units wide by thirty-two pixel units long, which is shown as the heavier vertical lines in the figure. Therefore, the interconnect 1824 between the substrates 1852 and 1854 must fall somewhere in the sixty-four pixel unit area in order to read that column. It should be noted that the aspect ratio of the support circuit area in this example is 2/32. Each pixel column is or may be one pixel wide and sixty-four pixels long and may have one read bus that runs from the top to the bottom of the pixel column. The choice of where to place the interconnect has many options within that area and could be chosen so as to allow the desired spacing from interconnect to interconnect. Moreover, because the interconnect can be located only where the pixel column read bus and the support circuit read bus superimpose, in order to read the corresponding pixel column the interconnect range may be one pixel wide and thirty-two pixels long (for this example), which is the intercept between the pixel column and the support circuit to be connected.

Figure 8:
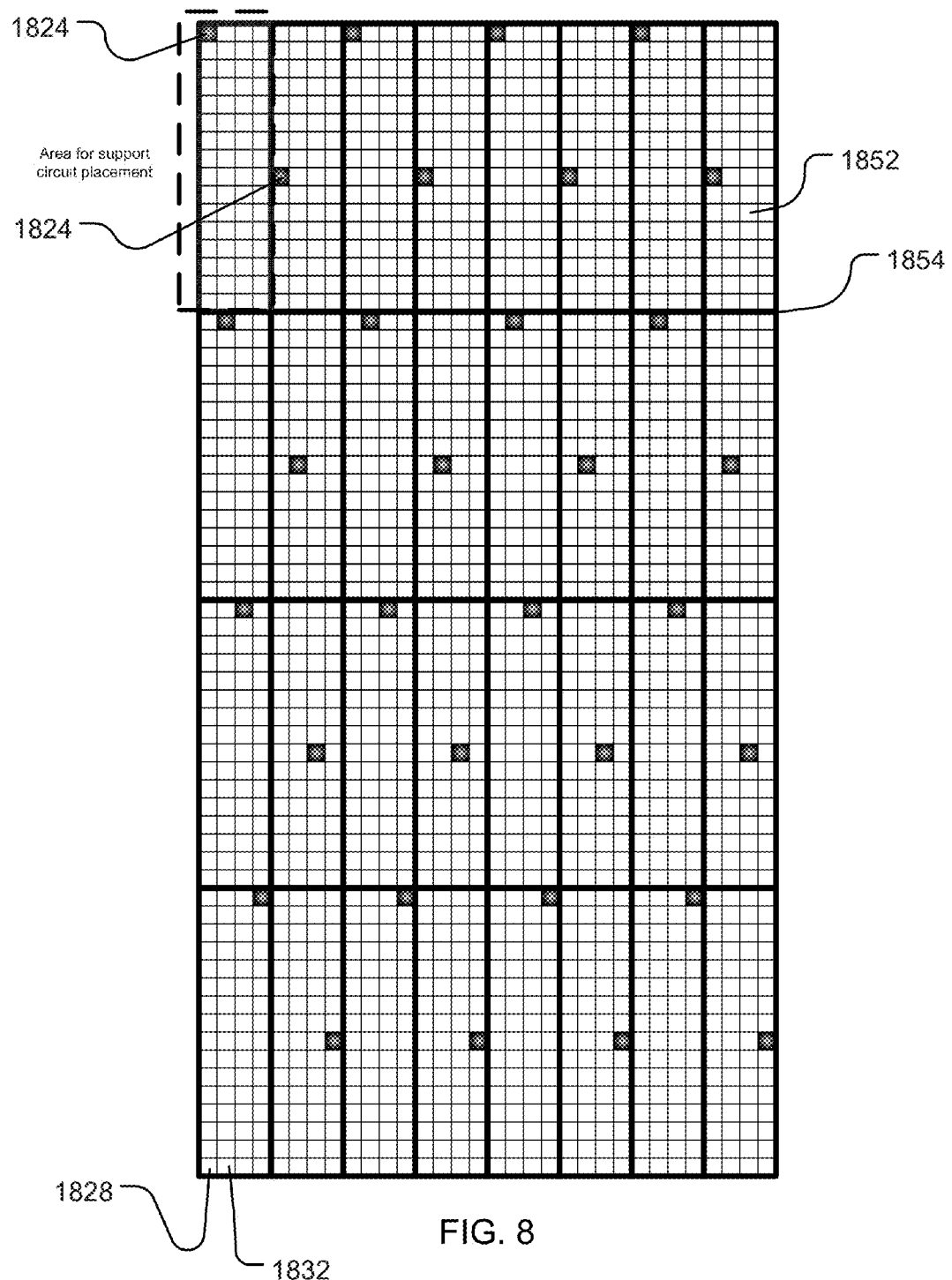

In FIG. 8, the area available for support circuit placement may be equal to four pixel units wide by sixteen pixel units long, which is shown as the heavier vertical lines in the figure. Therefore, the interconnect between the substrates must fall somewhere in the sixty-four pixel unit area in order to read the corresponding pixel column. It should be noted that the aspect ratio of the support circuit area in this example is 4/16. Each pixel column is or may be one pixel wide and sixty-four pixels long and may have one read bus that runs from the top to the bottom of the pixel column. The choice of where to place the interconnect has many options within that area and could be chosen so as to allow the desired spacing from interconnect to interconnect.

Moreover, because the interconnect can be located only where the pixel column read bus and the support circuit read bus superimpose, in order to read the corresponding pixel column the interconnect range may be one pixel wide and sixteen pixels long (for this example), which is the intercept between the pixel column and the support circuit to be connected.

Figure 9:
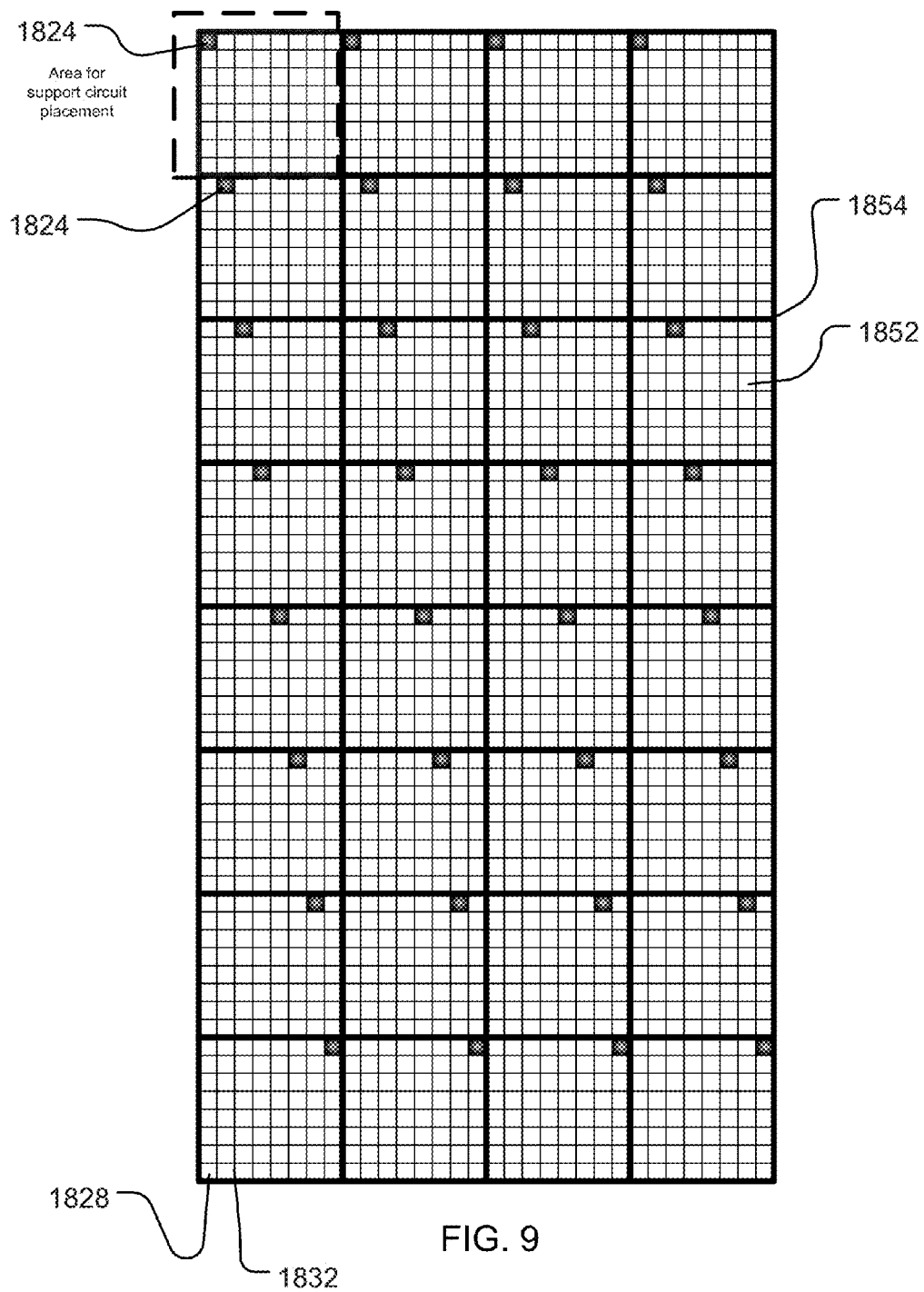

In FIG. 9, the area available for support circuit placement may be equal to eight pixel units wide by eight pixel units long, which is shown as the heavier vertical lines in the figure. Therefore, the interconnect 1824 between the substrates 1852 and 1854 must fall somewhere in the sixty-four pixel unit area in order to read the corresponding pixel column. It should be noted that the aspect ratio of the support circuit area in this example is 8/8. Each pixel column is or may be one pixel wide and sixty-four pixels long and may have one read bus that runs from the top to the bottom of the pixel column. The choice of where to place the interconnect has many options within that area and could be chosen so as to allow the desired spacing from interconnect to interconnect.

Moreover, because the interconnect can be located only where the pixel column read bus and the support circuit read bus superimpose, in order to read the corresponding pixel column the interconnect range may be one pixel wide and eight pixels long (for this example), which is the intercept between the pixel column and the support circuit to be connected.

Figure 10:
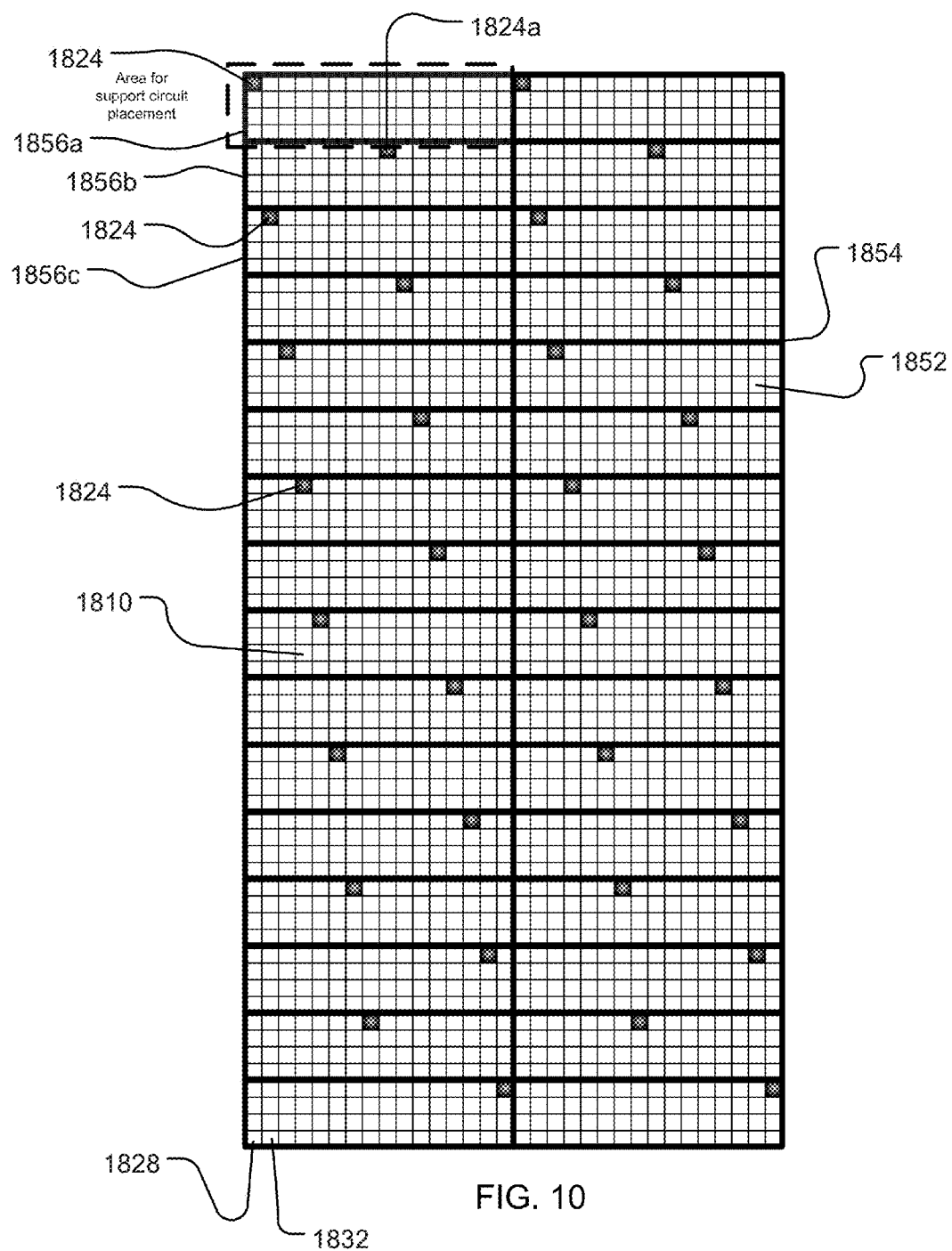

In FIG. 10, the area available for support circuit placement may be equal to sixteen pixel units wide by four pixel units long, which is shown as the heavier vertical lines in the figure. Therefore, the interconnect between the substrates must fall somewhere in the sixty-four pixel unit area in order to read the corresponding pixel column. It should be noted that the aspect ratio of the support circuit area in this example is 16/4, this example shows the flexibility that these methods and apparatuses disclosed herein can provide. Each pixel column is or may be one pixel wide and sixty-four pixels long and may have one read bus that runs from the top to the bottom of the pixel column. The choice of where to place the interconnect has many options within that area and could be chosen so as to allow the desired spacing from interconnect to interconnect.

Moreover, because the interconnect can be located only where the pixel column read bus and the support circuit read bus superimpose, in order to read the corresponding pixel column the interconnect range may be one pixel wide and four pixels long (for this example), which is the intercept between the pixel column and the support circuit to be connected.

It should also be noted that the pattern of the association of the support circuit to the pixel column may be different than that of FIGS. 6-10 and such association may ultimately provide the optimal distance of the interconnects away from each other. For example, the interconnects may be optimally placed at least two pixel widths apart, four pixel widths apart, eight pixel widths apart, or more from each other. A designer may optimally determine the distance that the interconnects may be placed apart from one another based on two degrees of freedom: (1) the number of pixels per column, and (2) the circuit aspect ratio and location. In the examples shown in FIGS. 6-10, the interconnects 1824 may be located about eight pixels away from each other. However, it will be understood that other designs may be implemented without departing from the spirit or scope of the disclosure. For example, as illustrated in FIG. 6, each of the interconnects 1824 may be located eight pixels in length and one pixel in width away from each other. Because the circuit columns each have an aspect ratio of one pixel in width and sixty-four pixels in length, the interconnects 1824 may then be located eight pixels away from each other in adjacent columns as illustrated in FIG. 6, until the bottom of the circuit 1800 is reached, in which case the interconnects 1824 are then moved to the top of the next column and continue for the entire width of the pixel array 1810. Conversely, in FIG. 10, the interconnects 1824 are still located eight pixels in length and one pixel in width away from each other. However, in this example, the circuit column aspect ratio is now four pixels in length and sixteen pixels in width. Thus, for the interconnects 1824 to be at least eight pixels away from each other, one circuit column 1856*b* must be skipped since the aspect ratio is only four pixels in length, such that the interconnects 1824 maintain optimal spacing. Thus, for example, placing an interconnect 1824 in the upper left corner of the pixel array 1810 in FIG. 10 (on the first pixel of the first column 1828) and then moving to the next pixel column 1832 and counting down eight pixels in length, the next interconnect 1824 may then be placed in the third circuit column 1856*c*, skipping the second circuit column 1856*b* altogether. This pattern may be used throughout the pixel array. The second, skipped circuit column 1856*b* is then connected to the pixel array by an interconnect 1824*a* that is placed in the ninth pixel column and the pattern is repeated for all skipped circuit columns. Thus, as illustrated, optimal interconnect spacing may be achieved and various circuit designs may be accommodated without departing from the scope of the disclosure.

Figure 11:
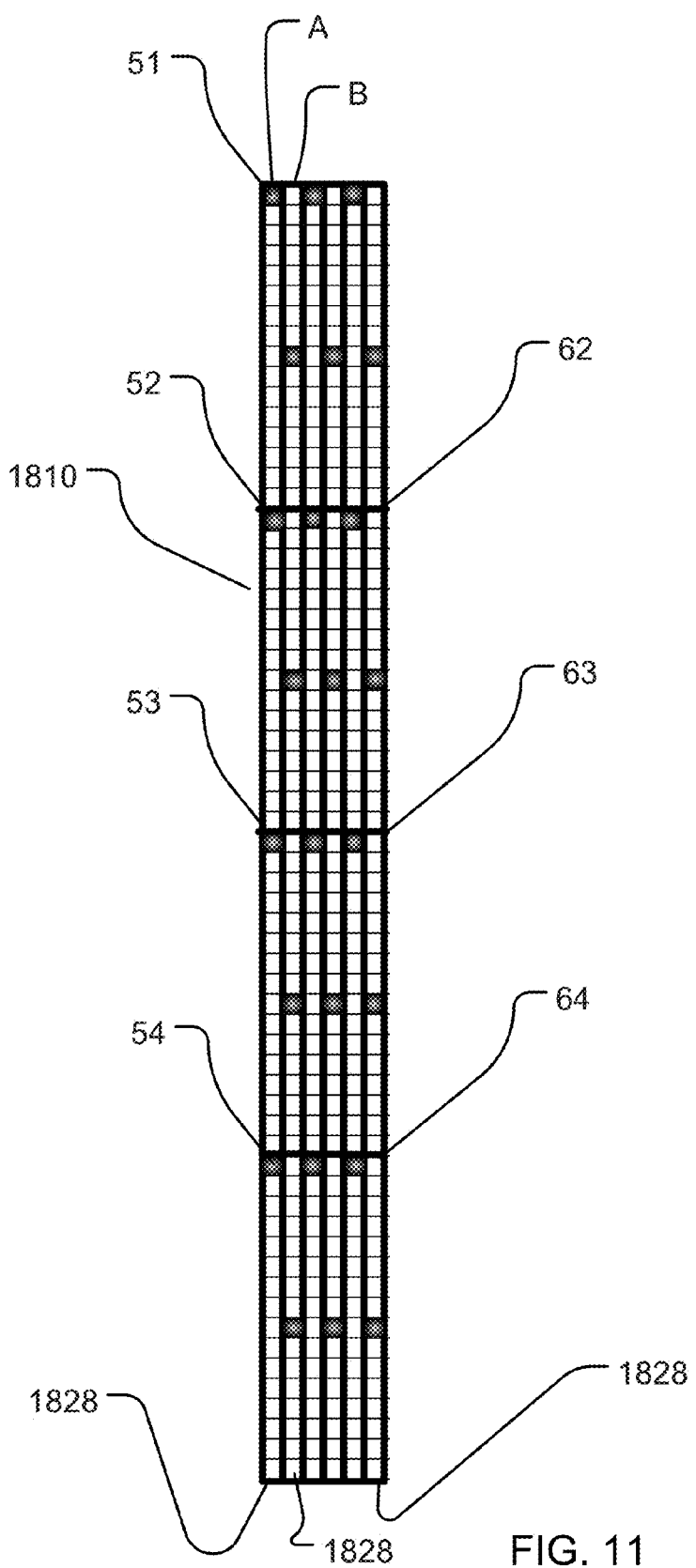
FIG. 11 illustrates a top view of an embodiment of an imaging sensor built on a plurality of substrates wherein a plurality of pixel columns and sub-columns forming the pixel array are located on the first substrate and a plurality of circuit columns are located on a second substrate and showing an electrical connection and communication between one column of pixels to its associated or corresponding column of circuitry.

Referring now to FIG. 11, a pixel array 1810 having columns and sub-columns will be discussed. As can be seen in FIG. 11, a portion of a pixel array 1810 is illustrated having six columns therein, each column running from the top of the portion of the pixel array illustrated to the bottom of the pixel array. It will be appreciated that the modern circuit 1800 will have a pixel array 1810 that comprises many more pixel columns (a plurality of pixels running in the Y-direction in the figure) and rows (a plurality of pixels running in the X-direction in the figure) forming the array 1810. Only a limited number of pixel columns and rows are shown herein for illustration purposes and for the sake of discussion and simplicity.

Each of the pixel columns 1828 in the pixel array 1810 may be divided into sub-columns. The sub-columns may be defined as a plurality of pixels within a column that is less than the entire column of pixels and that are electrically connected to a pixel sub-column bus. Thus, there may be a plurality of pixel sub-columns per pixel column 1828. Each of the sub-columns may have a contact pad and/or an interconnect illustrated as 51, 52, 53 and 54 to electrically connect each of the sub-column buses on the first substrate to an associated or corresponding circuit column bus located on the supporting substrate.

At least one pixel column bus may be used to provide an electrical connection for every pixel in the column 1828. The column 1828 may be divided into a plurality of sub-columns, where at least one pixel sub-column bus is present per pixel sub-column. The sub-column buses may be differentiated by dividers 62, 63, 64, which dividers may be a physical space or gap or other device for electrically isolating the pixel sub-column and/or sub-column bus from another sub-column and/or sub-column bus. During use, the data from the pixels may be read in a rolling type shutter manner, which is substantially simultaneous from each row of pixels in each of the sub-columns (illustrated as four sub-columns in FIG. 11). In such a configuration, the read time may be substantially reduced due to the number of sub-columns that are connected to dedicated circuit columns via the pixel sub-column read bus and the circuit column read bus and the interconnects that electrically connect the buses together. Thus, the read time in the embodiment illustrated may be theoretically reduced (i.e., reading speed is increased) for the entire column (which in FIG. 11 includes four sub-columns) by the number of sub-column buses. In FIG. 11, there are four sub-columns and sub-column buses, such that the read time is reduced (speed is increased by four times) by seventy-five percent. It will be appreciated that no matter the number or configuration of sub-columns, the rolling shutter may operate row by row at the beginning of each sub-column incrementally reading each pixel in the sub-column to the end of the sub-column simultaneously with the other sub-columns (simultaneously reading the row of pixels starting from the pixel row located at 51, 52, 53, 54).

In other embodiments, the column may be divided into any number of sub-columns, with each division of the column (e.g., addition of a sub-column) approximating a global shutter functionality. As can be seen in the figure, the contact pads and interconnect locations can be staggered in each of the columns. As illustrated, the interconnects from the column labeled "A" from those in the column labeled "B." Other iterations of sub-columns and interconnect staggering are possible for N number of columns.

Figure 12:
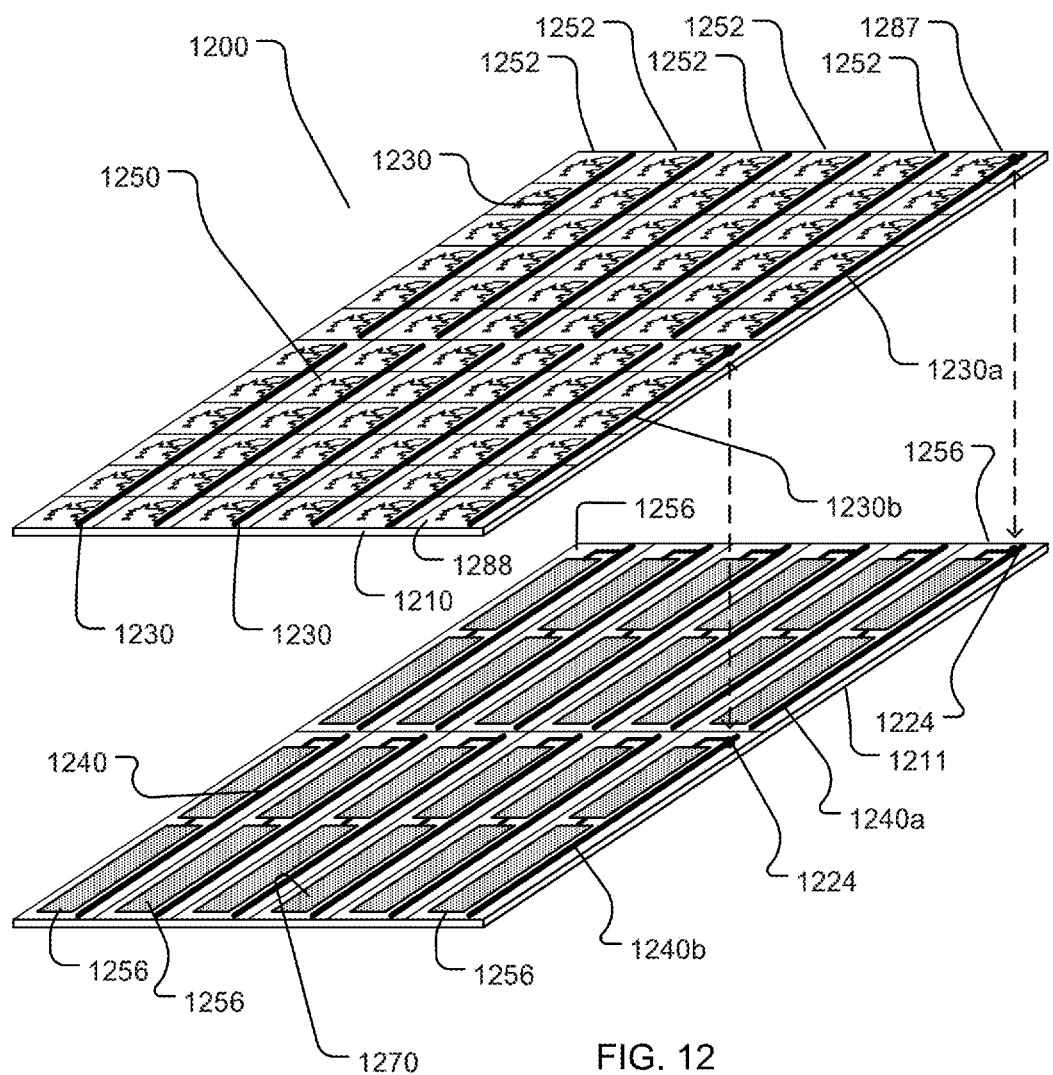
FIG. 12 illustrates a perspective view of an embodiment of a plurality of columns and sub-columns that together form a pixel array located on a first substrate and a plurality of circuit columns located on a second substrate and showing an electrical connection and communication between one sub-column of pixels to its associated or corresponding column of circuitry in accordance with the teachings and principles of the disclosure.
Figure 13:
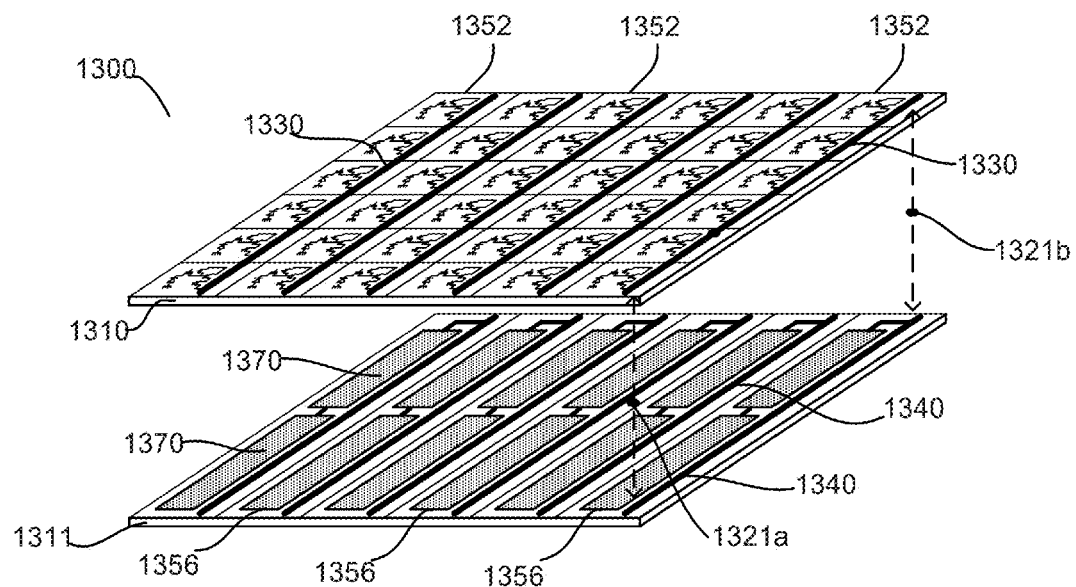
FIG. 13 illustrates a perspective view of an embodiment of a plurality of columns and sub-columns that together form a pixel array located on a first substrate and a plurality of circuit columns dedicated to one or more pixel sub-columns located on a second substrate and showing an electrical connection and communication between one column of pixels to its associated or corresponding column of circuitry in accordance with the teachings and principles of the disclosure.
Figure 14:
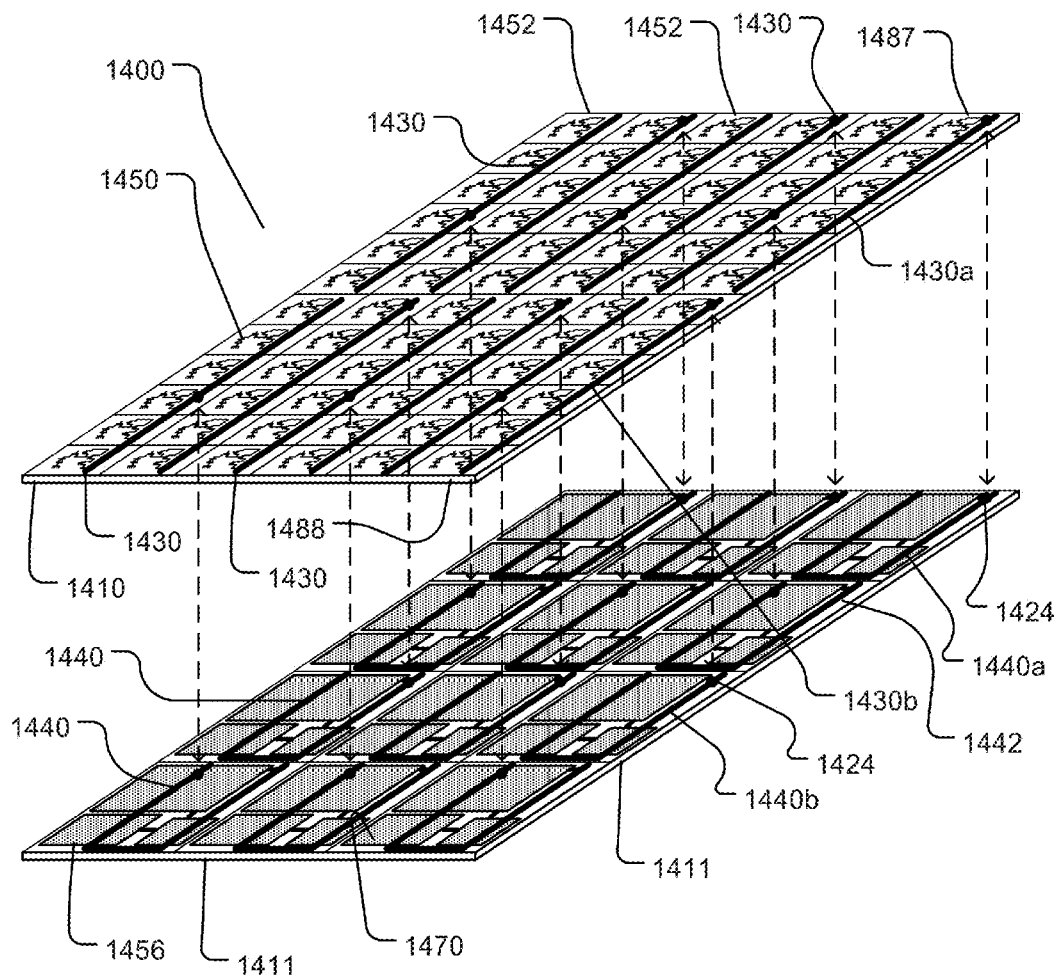
FIG. 14 illustrates a perspective view of an embodiment of a plurality of columns and sub-columns that together form a pixel array located on a first substrate and a plurality of circuit columns located on a second substrate and showing an electrical connection and communication between each sub-column of pixels to its associated or corresponding column of circuitry in accordance with the teachings and principles of the disclosure.

Referring now to FIGS. 12 through 14c, there is illustrated various views of an embodiment of an imaging sensor 1200 built on a plurality of substrates having sub-column read functionality and remotely located support circuits. FIGS. 12 and 14 illustrate a plurality of pixel columns 1252 and 1452 forming the pixel array 1250 and 1450 on the first substrate 1210, 1410 and a plurality of circuit columns 1256, 1456 (that represent the supporting circuitry 1270, 1470) on the second substrate 1211, 1411.

As illustrated in FIGS. 12-12c, a pixel array 1250 may be divided into a plurality of columns and sub-columns 1252. The size of the columns and sub-columns may, for example, be based on the size of the associated circuitry 1270 and circuit columns 1256. For example, the pixel sub-column 1252 may be one pixel in width and "N" number of pixels long (in FIGS. 12-12c, the pixel sub-columns are illustrated as being one pixel wide and six pixels long) and the circuit columns 1256 are illustrated as having an aspect ratio of one pixel wide by six pixels long. It will be appreciated that the size or area of the circuit column 1256 may dictate or direct the size of the pixel sub-column 1252, since the pixel sub-column 1252 should have substantially the same area as the circuit column 1256. The pixel sub-column 1252 may be directly associated with circuit column 1256 through an electrical connection between an interconnect 1224 that electrically connects the pixel read bus 1230 to the circuit read bus 1240. The figures show an example of a connection between each pixel sub-column 1252 to its associated circuitry 1270 in a circuit column 1256 through read buses 1230 and 1240.

The figures also show one read bus 1230 per pixel sub-column 1252 and one read bus 1240 per circuit column 1256. In this embodiment, the associated circuitry 1270 in a circuit column 1256 is one pixel wide and six pixels long, but it will be appreciated that any circuit column aspect ratio may be utilized by the disclosure. As can be seen in FIGS. 12-12c, the columns have all been divided into two sub-columns 1287, 1288. Accordingly, pixel column read bus 1230 may be manufactured into corresponding pixel sub-column read buses 1230a and 1230b. Each pixel sub-column 1287, 1288 may be connected to a pixel column bus 1230a or 1230b first and then to supporting circuitry 1270 and circuit column 1256, or each sub-column 1287, 1288 may connect directly to the circuitry 1270 and circuit column 1256 through their own interconnect 1224a and 1224b, respectively, to an associated circuit bus 1240a and 1240b.

As noted herein above, each pixel sub-column 1252 may be electrically associated or connected to one pixel sub-column bus 1230, and each circuit column 1256 may be electrically associated or connected to one circuit column bus 1240. FIGS. 12a-12c illustrate a perspective view, a front view and a side view, respectively, of a single pixel column 1252 divided into sub-columns 1287, 1288 and two associated circuit columns 1256 separated from the plurality of pixel columns 1252 and plurality of circuit columns 1256 illustrated in FIG. 12. As illustrated in FIGS. 12a-12c, there are two read buses 1230a, 1230b per pixel column, which thereby separates the column into two sub-columns. Two supporting circuits (one support circuit per pixel sub-column read bus. In this configuration, there is an aspect ratio of the circuit column is 6/1, the aspect ratio of the pixel sub-column is also 6/1, and the aspect ratio of the whole pixel column is 12/1.

FIG. 12a-12c also further illustrate the electrical connection between the pixel sub-column buses 1230a and 1230b of the pixel sub-columns 1287, 1288 and the circuit columns 1256 using one or more interconnects 1224 per sub-column connection. While the pixel sub-buses 1230a and 1230b and buses 1240a and 1240b may be electrically connected using one or more interconnects 1224, the figures illustrate that the interconnects 1224 may be located anywhere along the superimposed path of the pixel sub-buses 1230a and 1230b and buses 1240 without departing from the spirit or scope of the disclosure.

Figure 13A:
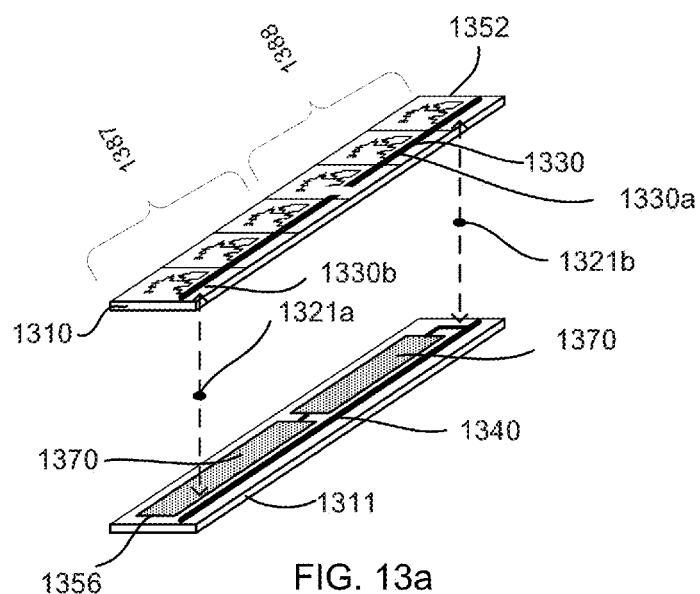
FIG. 13a illustrates a perspective view of a single column of pixels that have been formed into two separate sub-columns of pixels, wherein both pixel sub-columns are attached to a different pixel column read bus, and illustrating an electrical connection between the read buses to a column of circuitry taken from FIG. 13.

FIGS. 13 and 13a illustrate an alternative embodiment in which the pixel column has been divided into a plurality of sub-columns, each having their own bus. However, the sub-columns are illustrated as being connected by their individual buses to a single circuit column.

Similar to FIGS. 12-12c, FIGS. 14-14c illustrate a pixel array 1450 being divided into a plurality of columns and sub-columns 1452. The size of the columns and sub-columns may, for example, be based on the size of the associated circuitry 1470 and circuit columns 1456. For example, the pixel sub-column 1452 may be one pixel in width and "N" number of pixels long (in FIGS. 14-14c, the pixel sub-columns are illustrated as being one pixel wide and six pixels long, whereas the entire column is illustrated as being one pixel wide and twelve pixels long) and the circuit columns 1456 are illustrated as having an aspect ratio of two pixels wide by three pixels long. It will be appreciated that the size or area of the circuit column 1456 may dictate or direct the size of the pixel sub-column 1452, since the pixel sub-column 1452 should have substantially the same area as the circuit column 1456. The pixel sub-column 1452 may be directly associated with circuit column 1456 through an electrical connection between an interconnect 1424 that electrically connects the pixel read bus 1430 to the circuit read bus 1440. The figures show an example of a connection between each pixel sub-column 1452 to its associated circuitry 1470 in a circuit column 1456 through read buses 1430 and 1440.

Figure 14A:
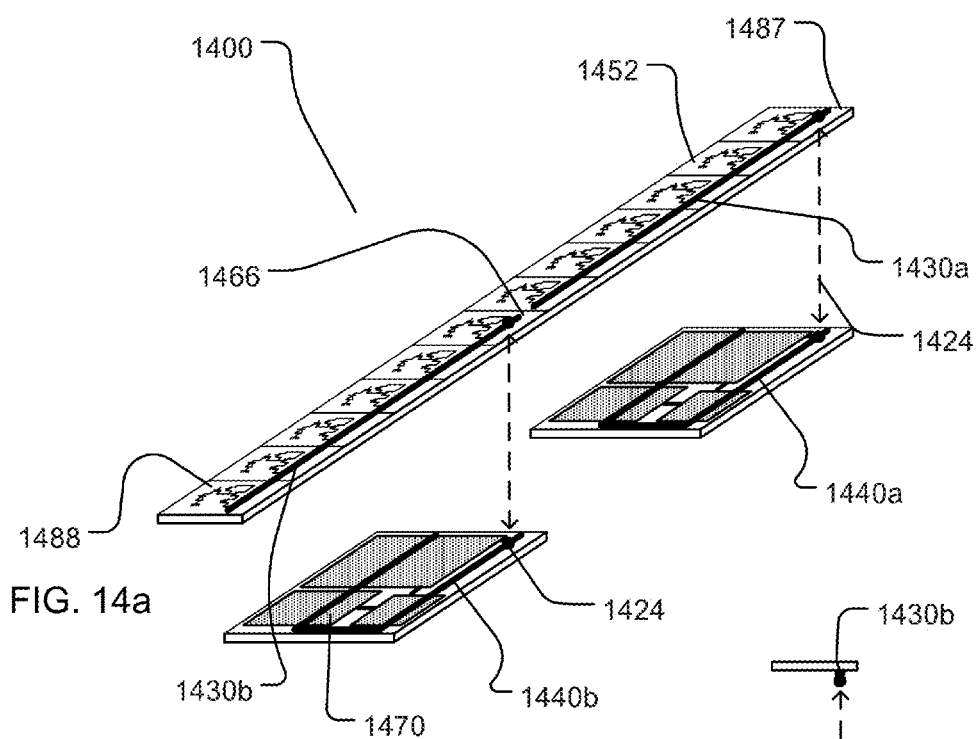
FIGS. 14a-14c illustrate perspective, front and side views, respectively, of a single column of pixels that have been formed into two separate sub-columns of pixels, wherein each pixel sub-column is attached to a different pixel column read bus, and illustrating two columns of circuitry taken from FIG. 14 showing an electrical connection therebetween.
Figure 14B:
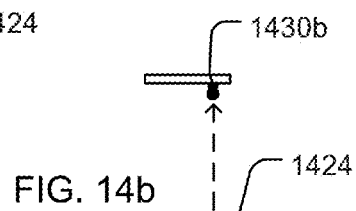
Figure 14C:
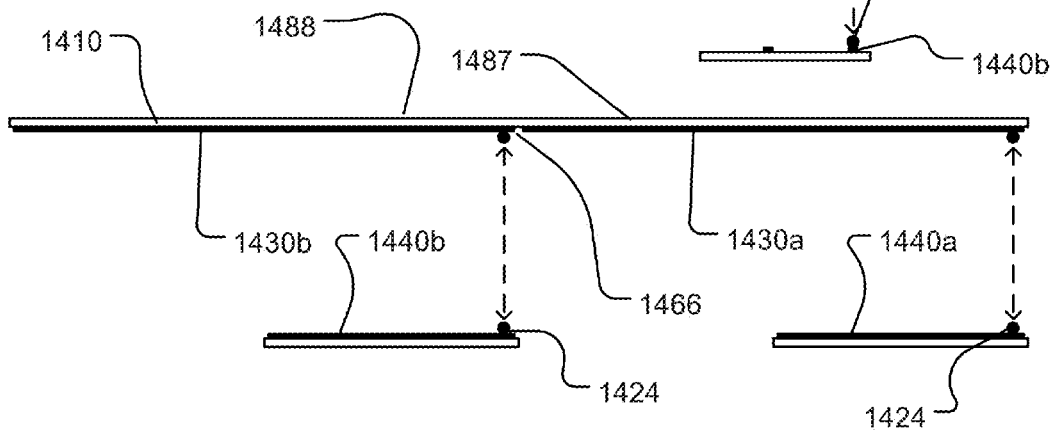

The figures also show one read bus 1430 per pixel sub-column 1452 and one read bus 1440 per circuit column 1456. In this embodiment, the associated circuitry 1470 in a circuit column 1456 is two pixels wide and three pixels long, but it will be appreciated that any circuit column aspect ratio may be utilized by the disclosure. As can be seen in FIGS. 14-14c, the columns have all been divided into two sub-columns 1487, 1488. Accordingly, pixel column read bus 1430 may be manufactured into corresponding pixel sub-column read buses 1430a and 1430b. Each pixel sub-column 1487, 1488 may be connected to a pixel column bus 1430a or 1430b first and then to supporting circuitry 1470 and circuit column 1456, or each sub-column 1487, 1488 may connect directly to the circuitry 1470 and circuit column 1456 through their own interconnect 1424a and 1424b, respectively, to an associated circuit bus 1440a and 1440b.

As noted herein above, each pixel sub-column 1452 may be electrically associated or connected to one pixel sub-column bus 1430, and each circuit column 1456 may be electrically associated or connected to one circuit column bus 1440. FIGS. 14a-14c illustrate a perspective view, a front view and a side view, respectively, of a single pixel column 1452 divided into sub-columns 1487, 1488 and two associated circuit columns 1456 separated from the plurality of pixel columns 1452 and plurality of circuit columns 1456 illustrated in FIG. 14. As illustrated in FIGS. 14a-14c, there are two read buses present for the entire pixel column. However, as illustrated the presence of the two read buses 1430a, 1430b are illustrated as being separate and distinct buses that are not electrically connected to each other, such that there is a separation or divider (as discussed above in relation to FIG. 11) that separates the column into two sub-columns. Accordingly, there may also be two supporting circuits and circuit column read buses (one support circuit and circuit column bus per pixel sub-column read bus). In this configuration, there is an aspect ratio of the circuit column is 3/2, the aspect ratio of the pixel sub-column is also 6/1, and the aspect ratio of the whole pixel column is 12/1.

FIG. 14a-14c further illustrate the electrical connection between the pixel sub-column buses 1430a and 1430b of the pixel sub-columns 1487, 1488 and the circuit columns 1456 using one or more interconnects 1424 per sub-column connection. While the pixel sub-buses 1430a and 1430b and circuit column buses 1440a and 1440b may be electrically connected using one or more interconnects 1424, the figures illustrate that the interconnects 1424 may be located anywhere along the superimposed path of the pixel sub-buses 1430a and 1430b and circuit column buses 1440 without departing from the spirit or scope of the disclosure.

FIGS. 14-14c also illustrate how differing aspect ratios between the substrates can allow for flexibility in bus contact points. In the embodiment, the column circuit bus 1440 has been designed with a general "u" shape that so as to occupy the area of the circuit column 1456 more evenly, thereby providing options for connecting the interconnect 1424 throughout the entire circuit column 1456. Note that the pixel column bus 1430 is not generally u-shaped, but the circuit column bus 1440 may be generally u-shaped, so that the same column circuit 1456 may be used with the two adjacent, but different pixel column configurations. The first leg of the u-shaped circuit column buses 1440a and 1440b may be superimposed to the read buses 1430a and 1430b of the pixel sub-columns 1487 and 1488 (as illustrated in FIG. 14a). The second leg of the u-shaped circuit column bus 1442 that is located between circuit column buses 1440a and 1440b may be superimposed to the read bus 1430 of the next, adjacent pixel column 1452 (as illustrated best in FIG. 14). FIGS. 14a-14c illustrate a single set of pixel sub-columns 1487 and 1488 taken from the pixel array 1450 of FIG. 14. It should be noted that because the aspect ratio of the circuit column 1456 is illustrated as being two pixels wide by three pixels long, which is one half the length of the corresponding pixel sub-columns 1487 and 1488, the interconnect 1424 location options are only available for a portion of the pixel sub-column length.

FIG. 14b illustrates that for a complex bus shape there may be two interconnect location path options along buses 1440a and 1440b in a circuit column 1456 having twice the width of the pixel sub-column 1487 and 1488 it supports. FIG. 14b illustrates a front view of the superimposition of the first leg of the u-shaped circuit column bus 1440b to the read bus 1430b of the pixel sub-column 1488 and uses the outer most portion of the bus 1440b for locating the interconnect 1424 as opposed to the innermost portion of the bus 1440b as illustrated in FIGS. 14 and 14a for locating the interconnect 1424 to the next, adjacent pixel column 1452.

FIG. 14 illustrates the next pixel sub-column 1452 located to the left of and relative to the pixel sub-columns 1487 and 1488 illustrated in FIGS. 14a-14c. The bus 1430 of the next pixel sub-column 1452 illustrated in FIG. 14 may be electrically connected to a different circuit bus 1442 that may be located between circuit bus 1440a and 1440b as illustrated. It should be noted that because the footprint of the circuit column 1456 has an aspect ratio of 2 pixels wide by 3 pixels long, the superimposition of the pixel sub-column bus 1430 to the circuit column bus 1442 requires the second leg of the circuit column bus 1442 to be generally u-shaped to thereby allow a natural match or superimposition of the bus 1442 with respect to the next pixel sub-column 1452 and its corresponding bus (with respect to the sub-column 1487) illustrated in FIG. 14.

Figure 15:
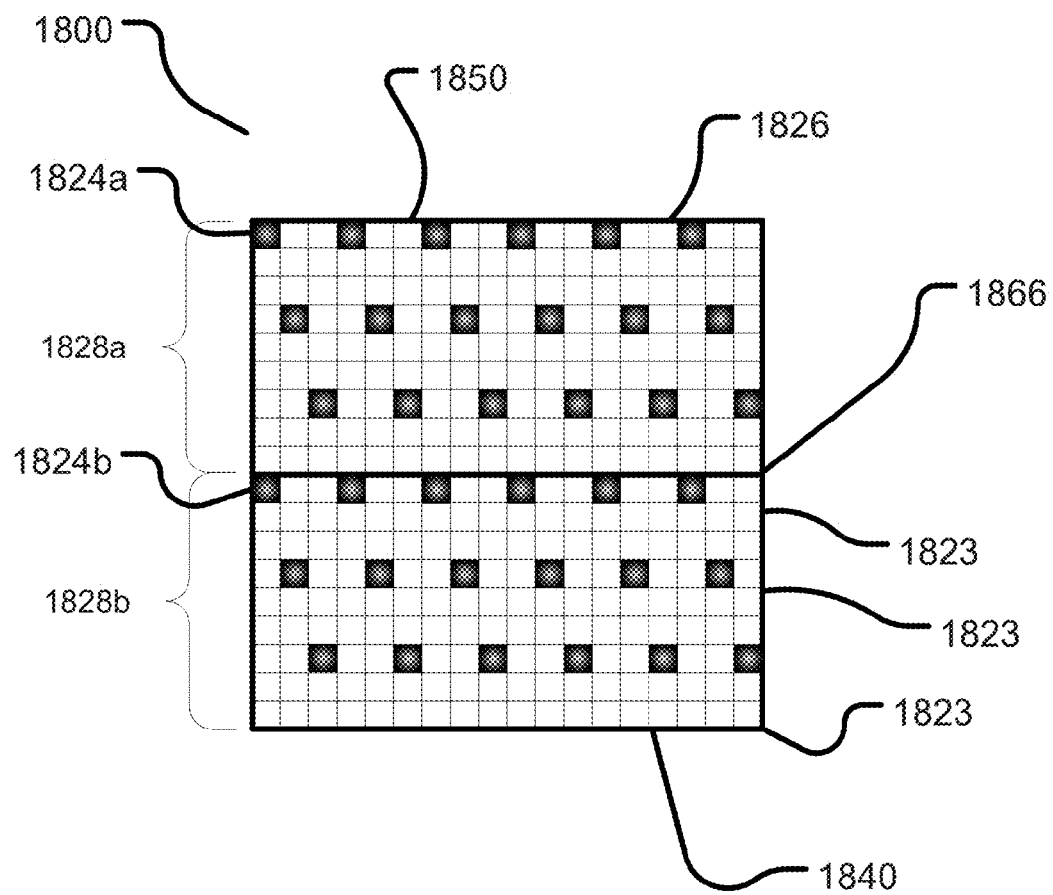
FIGS. 15-18 illustrate top views of various embodiments of a plurality of columns and sub-columns that together form a pixel array located on a first substrate and a plurality of circuit columns located on a second substrate and showing an electrical connection and communication between each sub-column of pixels to its associated or corresponding column of circuitry in accordance with the teachings and principles of the disclosure.

FIG. 15 illustrates an embodiment and configuration of a pixel array 1810 having staggered interconnect or bump 1824 positioning and sub-columns on a substrate/chip. As noted above, because there is one read bus per pixel column 1828 (or sub-column) and one read bus per circuit column, and because the read buses run from the top of the column to the bottom of the column, and because the pixel columns may be divided into sub-columns each having their own pixel column bus, the interconnect/bump 1824 may be placed anywhere along the superimposed path of the sub-column bus and the circuit column bus. In the figure, a divider 1866, which may be a physical space or gap or some other device for electrically isolating the pixel sub-column and/or sub-column bus from another sub-column and/or sub-column bus, divides the pixel column bus into pixel sub-column buses.

As can be seen in FIG. 15, a first sub-column 1828a of pixels 1826 may be electrically connected to its corresponding circuit column 1856 via a first interconnect 1824a that is connected to the buses 1830 and 1840, and a second sub-column 1828b by a second interconnect 1824b in a similar manner. In the embodiment, the second pixel column may be electrically accessed through a second set of sub column interconnects, which has been positioned during manufacture in a sub-column configuration relative to said first column interconnects. As illustrated, the location or position of the second interconnect may be two pixel widths away from the position of the first interconnect in both the X and Y dimensions or directions. A third set of interconnects may then be positioned in like manner in a third pixel column and so on for N-number of interconnect sets across the pixel array 1810.

Figure 16:
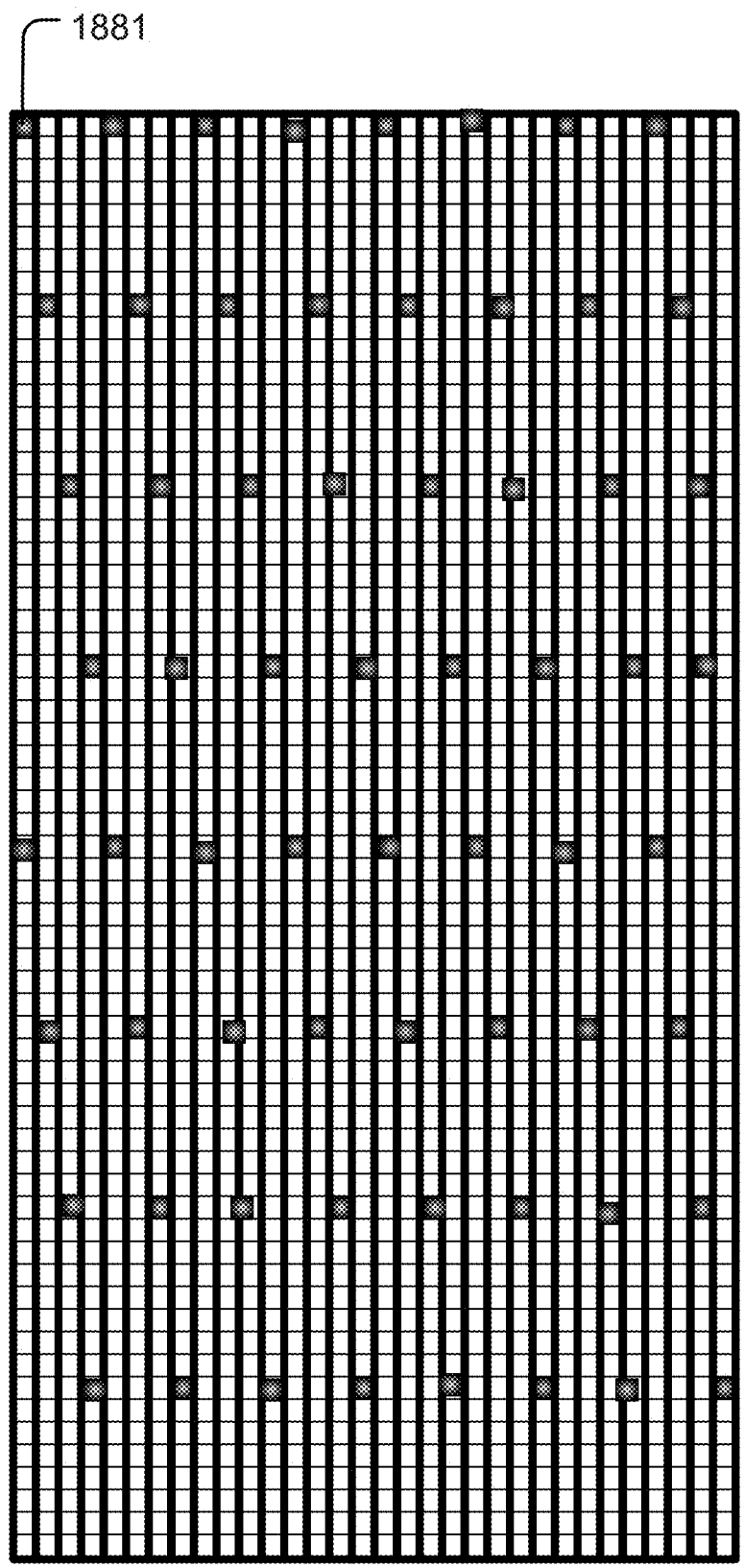

FIG. 16 illustrates a pixel array that is configured into such that each column is divided into two sub-columns and then staggered. The area available for locating support circuits for a first pixel column 1881 correlates to the pixel sub-column configuration as described above. As discussed further above, the support circuit area directly correlates to the area of a pixel column to which it corresponds. In FIG. 16 the area available for support circuit placement may be equal to one pixel unit wide by sixty-four pixel units long, which is shown as the heavier vertical lines in the figure. Additionally, each circuit column may correlate to one of the sub-columns or, in the alternative, the circuit column may also be in a manner that corresponds to the pixel column.

It should be noted that the exemplary aspect ratio of the support circuit area in FIG. 16 is illustrated as 1/64. There are many options to locate or place the interconnects for the sub-columns within that area and the ultimate location may then be chosen by the designer so as to allow the desired spacing from interconnect to interconnect.

Figure 17:
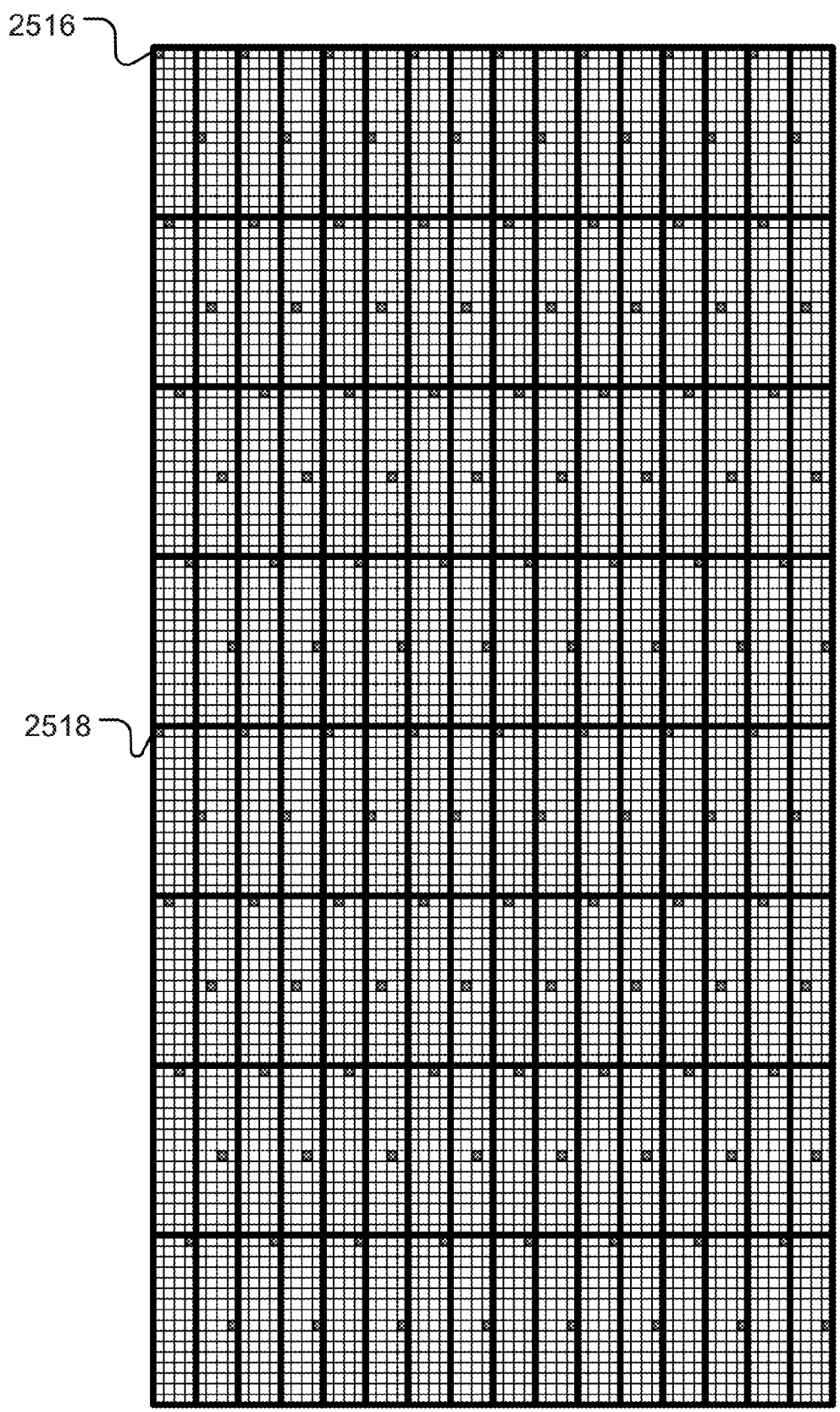

In FIG. 17 illustrates a schematically large image sensor showing the scalability of the principles and teaching of the disclosure. As can be seen in the figure, the area available for support circuit placement may be equal to four pixel units wide by sixteen pixel units long, which is shown as the heavier vertical lines in the figure. As illustrated there may be a plurality of interconnects 2516 and 2518 per pixel column denoting the pixel sub-columns so as to allow for more sub-column functionality for large array configurations. Therefore, the interconnect between the substrates must fall somewhere in the sub-column pixel unit areas in order to read the corresponding pixel column. It should be noted that the aspect ratio of the support circuit area in this example is 4/16, the sub column aspect ratio is 1/64 and the pixel column is 1/128. Therefore there are pixel sub-columns per pixel column. In this example, the frame read time (one rolling cycle) is half than that of what would be if this array would be not divided. There are two row addressing at the same time. The whole pixel array can be regarded as two independent, self consistent sub-arrays. Such in embodiment lends itself to support circuitry that directly corresponds to the pixel sub-columns. The choice of where to place the interconnect has many options within that area and could be chosen so as to allow the desired spacing from interconnect to interconnect. As the figure illustrates, by repeating the methods of this disclosure even the latest imaging sensor technology can be used with these methods.

Figure 18:
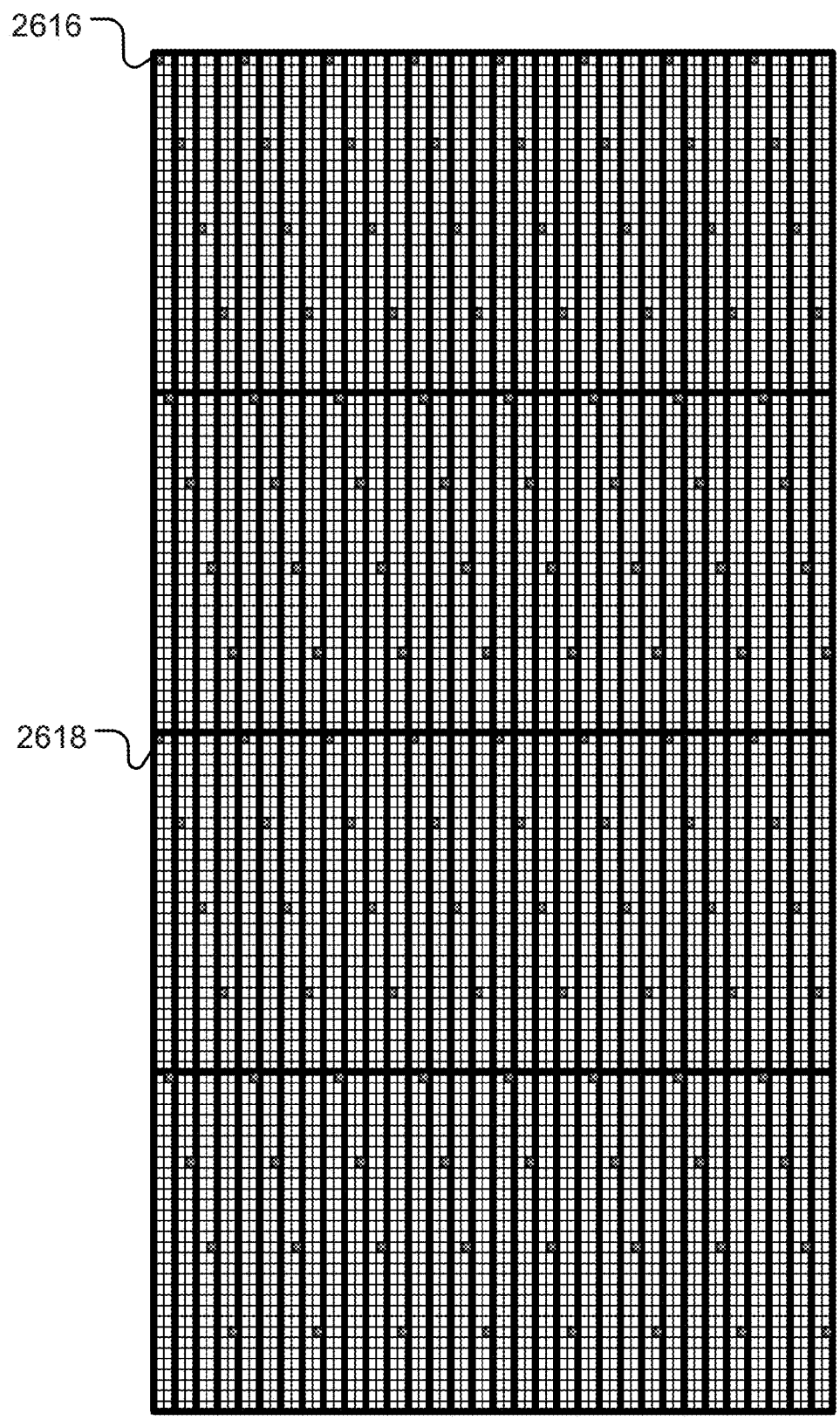

In FIG. 18 illustrates a schematically large image sensor showing the scalability of the principles and teaching of the disclosure. The plurality of interconnects 2616, 2618 per column indicate that the pixel column has been divided into sub-columns. As can be seen in the figure, the area available for support circuit placement for the pixel sub-columns may be equal to two pixel units wide by thirty-two pixel units long, which is shown as the heavier vertical lines in the figure. Therefore, the interconnect between the substrates must fall somewhere in the sixty-four pixel unit area in order to read the corresponding pixel sub-columns. It should be noted that the aspect ratio of the support circuit area is 2/32. The choice of where to place the interconnect has many options within that area and could be chosen so as to allow the desired spacing from interconnect to interconnect. As the figure illustrates, by repeating the methods of this disclosure even the latest imaging sensor technology can be used with these methods.

It will be appreciated that the structures and apparatuses disclosed herein are merely exemplary for optimizing an imaging sensor, and it should be appreciated that any structure, apparatus or system for optimizing an image sensor, which performs functions the same as, or equivalent to, those disclosed herein are intended to fall within the scope of this disclosure, including those structures, apparatuses or systems for imaging, which are presently known, or which may become available in the future. Anything which functions the same as, or equivalently to, a means for optimizing an imaging sensor falls within the scope of this disclosure.

Those having ordinary skill in the relevant art will appreciate the advantages provide by the features of the disclosure. For example, it is a potential feature of the disclosure to provide an optimized imaging sensor, which is simple in design and manufacture. Another potential feature of the disclosure is to provide such an imaging sensor with larger pixels relative to overall size.

In the foregoing Detailed Description, various features of the disclosure are either grouped together in a single embodiment for the purpose of streamlining the disclosure or are discussed in different embodiments. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment and various inventive features disclosed in separate embodiments may be combined to form its own embodiment as claimed more fully below. Thus, the following claims are hereby incorporated into this Detailed Description by this reference, with each claim standing on its own as a separate embodiment of the disclosure.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An imaging sensor comprising:
    a plurality of substrates;
    a pixel array comprising pixels formed into a plurality of pixel columns, wherein each of said plurality of pixel columns is divided into a plurality of pixel sub-columns that are independent and distinct, wherein each pixel sub-column comprises a plurality of pixels, wherein each pixel sub-column has a pixel sub-column bus;
    a plurality of supporting circuits formed into a plurality of supporting circuit columns, wherein each of said plurality of supporting circuit columns is divided into a plurality of circuit sub-columns that are independent and distinct, wherein each circuit sub-column has a circuit bus, wherein one pixel sub-column bus corresponds with one circuit bus;
    wherein a first substrate of the plurality of substrates comprises the pixel array;
    wherein the plurality of supporting circuits is disposed on a second substrate that is disposed remotely relative to said first substrate;
    wherein each of said plurality of circuit sub-columns is electrically connected to, and in electrical communication with, a corresponding pixel sub-column of said pixel array; and
    wherein said electrical communication is provided by an interconnect for each pixel sub-column bus and corresponding circuit bus disposed between said first substrate and said second substrate, such that each of the pixel sub-columns is read independently.

2. The imaging sensor of claim 1, wherein each pixel sub-column bus and each circuit bus are superimposed, such that each pixel sub-column bus and each circuit bus are substantially aligned; and
    wherein the interconnect is located anywhere along the superimposed pixel sub-column bus and circuit bus.

3. The imaging sensor of claim 2, wherein the electrical connection between one pixel sub-column bus and one circuit bus is accomplished by a plurality of interconnects.

4. The imaging sensor of claim 1, wherein said imaging sensor is backside illuminated.

5. The imaging sensor of claim 1, wherein the plurality of substrates further comprise a plurality of subsequent supporting substrates.

6. The imaging sensor of claim 1, wherein each pixel sub-column is electronically isolated from other pixel sub-columns.

7. The imaging sensor of claim 1, wherein said second substrate comprises support circuits dedicated and corresponding to each pixel sub-column of the pixel array.

8. The imaging sensor of claim 1, wherein said pixel sub-columns are electrically configured to be read at substantially the same time.

9. A method of accessing data on an imaging sensor comprising:
   electronically connecting pixels in a pixel array located on a first substrate to support circuits on a second substrate;
      wherein said pixel array is organized into pixel columns;
      wherein each of said pixel columns is divided into a plurality of pixel sub-columns that are independent and distinct, wherein each pixel sub-column comprises a plurality of pixels, wherein each pixel sub-column has a pixel sub-column bus;
   reading the plurality of pixel sub-columns starting with a first pixel in each sub-column and sequentially reading pixel data from each of the pixels until the last pixel in the sub-column is read;
   transmitting said pixel data for each pixel sub-column through an interconnect to a corresponding circuit sub-column located on the second substrate, wherein the second substrate comprises a plurality of circuit columns, wherein each of said plurality of circuit columns is divided into a plurality of circuit sub-columns that are independent and distinct, wherein each circuit sub-column has a circuit bus, wherein one pixel sub-column bus corresponds with one circuit bus;
      wherein the data from each pixel sub-column is processed by the circuit sub-column corresponding with each of said pixel sub-column,
   processing said pixel data into an image.

10. The method of accessing data on an imaging sensor of claim 9, further comprising reading pixel data from each pixel sub-column simultaneously.

11. The method of accessing data on an imaging sensor of claim 9, further comprising transmitting said pixel data to a support circuit that corresponds to a plurality of pixel sub-columns from within the same pixel column.

12. An imaging sensor comprising:
   a plurality of substrates comprising at least a first substrate and a second substrate;
   a pixel array located on the first substrate and comprising a plurality of pixel columns, wherein each of the plurality of pixel columns is defined as a plurality of pixels in length enough to cover the dimension of the array;
   wherein each of said pixel columns is divided into a plurality of pixel sub-columns, wherein each pixel sub-column comprises a plurality of pixels, such that each pixel sub-column is electrically isolated from other pixel sub-columns;
   a plurality of supporting circuits located on the second substrate and comprising a plurality of circuit columns, wherein the plurality of circuit columns is divided into a plurality of circuit sub-columns that are independent and distinct where one circuit sub-column corresponds with one pixel sub-column, wherein each of the plurality of circuit sub-columns is defined as having an area and size that corresponds with an area and size of a corresponding pixel sub-column;
   a plurality of buses, wherein there is one pixel sub-column bus per at least one pixel sub-column residing on the first substrate and one circuit column bus per at least one circuit sub-column residing on said second substrate;
   wherein at least a portion of each of the pixel sub-column buses is superimposed with at least a portion of each of the corresponding circuit column buses and at least one interconnect providing electrical communication between one pixel sub-column bus and one corresponding circuit column bus; and
   wherein said at least one interconnect is located anywhere along the superimposition of the pixel sub-column bus and the corresponding circuit column bus.

13. The imaging sensor of claim 12, further comprising a plurality interconnects disposed between said substrates and wherein said plurality of interconnects are spaced relative to one another at a distance that is greater than a pixel pitch of said pixel array.

14. The imaging sensor of claim 12, wherein the first substrate and second substrate are in alignment.

15. The imaging sensor of claim 12, wherein an area of one of said pixel sub-columns on said first substrate is substantially equal to an area of one of said corresponding circuit sub-columns on said second substrate.

16. The imaging sensor of claim 12, wherein said second substrate is substantially the same size as said first substrate.

17. The imaging sensor of claim 12, wherein an area of one of said pixel sub-columns on said first substrate is larger than an area of one of said corresponding circuit sub-columns on said second substrate.

18. The imaging sensor of claim 12, wherein an area of one of said pixel sub-columns on said first substrate is smaller than an area of one of said corresponding circuit sub-columns on said second substrate.

19. The imaging sensor of claim 12, wherein an aspect ratio of one of said pixel sub-columns is substantially similar to an aspect ratio of one of said circuit sub-columns.

20. The imaging sensor of claim 12, wherein a plurality of interconnects connect a pixel sub-column bus to a corresponding circuit column bus.

21. The imaging sensor of claim 12, wherein an aspect ratio of one of said pixel sub-columns is different than an aspect ratio of one of said circuit sub-columns.

22. The imaging sensor of claim 12, wherein the aspect ratio of at least one of said circuit sub-columns is "N" pixels wide and 1/"M" pixels in length of the aspect ratio of one of said pixel sub-columns.

23. The imaging sensor of claim 12, wherein the aspect ratio of at least one of said circuit sub-columns is two times wider than and one-half the length of the aspect ratio of one of said pixel sub-columns.

24. The imaging sensor of claim 12, wherein the aspect ratio of at least one of said circuit sub-columns is four times wider than and one-fourth the length of the aspect ratio of one of said pixel sub-columns.

25. The imaging sensor of claim 12, wherein the aspect ratio of at least one of said circuit sub-columns is eight times wider than and one-eighth the length of the aspect ratio of one of said pixel sub-columns.

26. The method of accessing data on an imaging sensor of claim 9, further comprising transmitting said pixel data from one of the plurality of pixel sub-columns to a support circuit having a support circuit area and size that is the same as the pixel sub-column area and size.

27. An imaging sensor comprising:
   a plurality of substrates comprising a first substrate and a second, supporting substrate;
   a pixel array comprising pixels formed into pixel columns, wherein each of the pixel columns is divided into a plurality of pixel sub-columns that are independent and distinct, wherein each pixel sub-column comprises a plurality of pixels, wherein each pixel sub-column has a corresponding pixel sub-column bus;
   a plurality of supporting circuits formed into a plurality of supporting circuit columns, wherein each of the supporting circuit columns is divided into a plurality of circuit sub-columns that are independent and distinct, wherein each circuit sub-column has a corresponding circuit bus, wherein one pixel sub-column bus corresponds with one circuit bus;

wherein the first substrate comprises the pixel array and the pixel sub-column buses;

wherein the second, supporting substrate is disposed remotely relative to the first substrate and comprises the plurality of supporting circuits and the circuit buses;

wherein each of the circuit sub-columns is electrically connected to, and in electrical communication with, a corresponding pixel sub-column of the pixel array; and wherein the electrical communication is provided by a single interconnect for each pixel sub-column bus and corresponding circuit bus disposed between the first substrate and the second, supporting substrate such that each of the pixel sub-columns is read independently.

* * * * *